United States Patent
Reis

(10) Patent No.: US 7,922,693 B2
(45) Date of Patent: Apr. 12, 2011

(54) APPARATUS SYSTEMS AND METHODS FOR FLUSHING GAS FROM A CATHETER OF A ROBOTIC CATHETER SYSTEM

(75) Inventor: Gene Reis, Mountain View, CA (US)

(73) Assignee: Hansen Medical, Inc., Mountain View, CA (US)

( * ) Notice: Subject to any disclaimer, the term of this patent is extended or adjusted under 35 U.S.C. 154(b) by 42 days.

(21) Appl. No.: 12/077,736

(22) Filed: Mar. 19, 2008

(65) Prior Publication Data

US 2008/0234631 A1 Sep. 25, 2008

Related U.S. Application Data

(60) Provisional application No. 60/919,015, filed on Mar. 19, 2007.

(51) Int. Cl.
*A61M 1/00* (2006.01)

(52) U.S. Cl. ........................................ 604/119; 604/118

(58) Field of Classification Search .......... 604/118–122, 604/151–155, 246–256; 600/431–435
See application file for complete search history.

(56) References Cited

U.S. PATENT DOCUMENTS

| | | | |
|---|---|---|---|
| 4,645,496 A * | 2/1987 | Oscarsson | 604/248 |
| 4,771,772 A * | 9/1988 | DeWitt | 604/892.1 |
| 4,819,653 A * | 4/1989 | Marks | 600/486 |
| 5,356,375 A | 10/1994 | Higley | |
| 2002/0183651 A1 | 12/2002 | Hyun | |
| 2002/0198560 A1 | 12/2002 | Boyle et al. | |
| 2004/0176751 A1 * | 9/2004 | Weitzner et al. | 606/1 |
| 2006/0084945 A1 | 4/2006 | Mill et al. | |
| 2006/0095022 A1 * | 5/2006 | Moll et al. | 606/1 |
| 2007/0016174 A1 * | 1/2007 | Millman et al. | 606/1 |
| 2007/0197896 A1 * | 8/2007 | Moll et al. | 600/407 |
| 2007/0197939 A1 * | 8/2007 | Wallace et al. | 600/587 |

FOREIGN PATENT DOCUMENTS

EP 0635279 1/1995

OTHER PUBLICATIONS

PCT Written Opinion of the International Search Authority for PCT/US2008/003709, Applicant Hansen Medical, Inc, Form PCT/ISA210, dated Jan. 5, 2009 (16 pages).

* cited by examiner

*Primary Examiner* — Nicholas D Lucchesi
*Assistant Examiner* — Gerald Landry, II
(74) *Attorney, Agent, or Firm* — Levine Bagade Han LLP

(57) ABSTRACT

Apparatus, systems and methods for flushing a lumen of a catheter instrument to reduce or eliminate bubbles within the lumen. An interface valve is adapted for attachment to a proximal end of the catheter instrument and can receive a working instrument for insertion into the catheter instrument lumen. A fluid supply line and purge lines are coupled to the interface valve and in fluid communication with at least a portion of the interface valve lumen. Flow of fluid (e.g. saline and a gas such as bubbles) through purge lines is controllable using clamps such that fluid flowing into the interface valve lumen can be manipulated to flow in different directions through different portions of the interface valve lumen for evacuation through different purge lines, thus allowing for purging of forward and backward flows to remove gas or bubbles from the catheter instrument lumen.

15 Claims, 30 Drawing Sheets

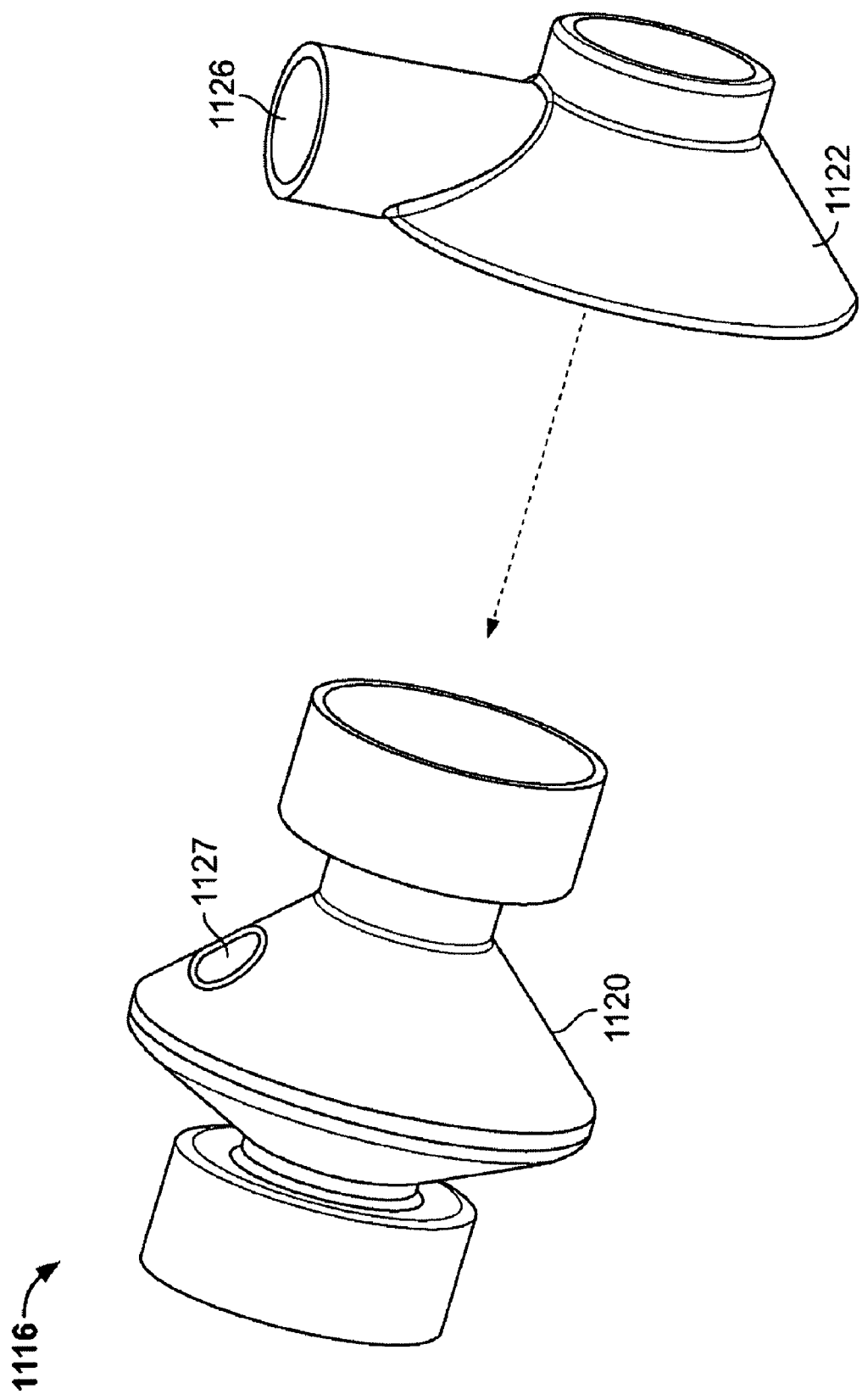

APPARATUS SYSTEMS AND METHODS FOR FLUSHING GAS FROM A CATHETER OF A ROBOTIC CATHETER SYSTEM

CROSS-REFERENCE TO RELATED APPLICATION

The present application claims the benefit under 35 U.S.C. §119 to U.S. Provisional Application No. 60/919,015, filed on Mar. 19, 2007, the contents of which are incorporated herein by reference as though set forth in full.

The present application may also be related to subject matter disclosed in the following applications and patents, the contents of which are also incorporated herein by reference as though set forth in full: U.S. Provisional Application No. 60/920,328, entitled "Robotic Catheter Systems and Methods," filed Mar. 26, 2007; U.S. patent application Ser. No. 10/923,660, entitled "System and Method for 3-D Imaging", filed Aug. 20, 2004; U.S. patent application Ser. No. 10/949,032, entitled "Balloon Visualization for Transversing a Tissue Wall", filed Sep. 24, 2005; U.S. patent application Ser. No. 11/073,363, entitled "Robotic Catheter System", filed Mar. 4, 2005; U.S. patent application Ser. No. 11/173,812, entitled "Support Assembly for Robotic Catheter Assembly", filed Jul. 1, 2005; U.S. patent application Ser. No. 11/176,954, entitled "Instrument Driver for Robotic Catheter System", filed Jul. 6, 2005; U.S. patent application Ser. No. 11/179,007, entitled "Methods Using A Robotic Cather System", filed Jul. 6, 2005; U.S. patent application Ser. No. 11/185,432, entitled "System and method for denaturing and fixing collagenous tissue", filed Jul. 19, 2005; U.S. patent application Ser. No. 11/202,925, entitled "Robotically Controlled Intravascular Tissue Injection System", filed Aug. 12, 2005; U.S. Provisional Patent Application No. 60/750,590, entitled "Robotic Catheter System and Methods", filed Dec. 14, 2005; U.S. Provisional Patent Application No. 60/756,136, entitled "Robotic Catheter System and Methods", filed Jan. 3, 2006; U.S. patent application Ser. No. 11/331,576, entitled "Robotic Catheter System", filed Jan. 13, 2006; U.S. Provisional Patent Application No. 60/776,065, entitled "Force Sensing for Medical Instruments", filed Feb. 22, 2006; U.S. Provisional Patent Application No. 60/785,001, entitled "Fiberoptic Bragg Grating Medical Instrument", filed Mar. 22, 2006; U.S. Provisional Patent Application No. 60/788,176, entitled "Fiberoptic Bragg Grating Medical Instrument", filed Mar. 31, 2006; U.S. patent application Ser. No. 11/418,398, entitled "Robotic Catheter System", filed May 3, 2006; U.S. Provisional Patent Application No. 60/801,355, entitled "Sheath and Guide Catheter Apparatuses For A Robotic Catheter System With Force Sensing", filed May 17, 2006; U.S. Provisional Patent Application No. 60/801,546, entitled "Robotic Catheter System and Methods", filed May 17, 2006; U.S. Provisional Patent Application No. 60/801,945, entitled "Robotic Catheter System and Methods", filed May 18, 2006; U.S. patent application Ser. No. 11/481,433, entitled "Robotic Catheter System and Methods", filed Jul. 3, 2006; U.S. Provisional Patent Application No. 60/833,624, entitled "Robotic Catheter System and Methods", filed Jul. 26, 2006; U.S. Provisional Patent Application No. 60/835,592, entitled "Robotic Catheter System and Methods", filed Aug. 3, 2006; U.S. Provisional Patent Application No. 60/838,075, entitled "Robotic Catheter System and Methods", filed Aug. 15, 2006; U.S. Provisional Patent Application No. 60/840,331, entitled "Robotic Catheter System and Methods", filed Aug. 24, 2006; U.S. Provisional Patent Application No. 60/843,274, entitled "Robotic Catheter System and Methods", filed Sep. 8, 2006; U.S. Provisional Patent Application No. 60/873,901, entitled "Robotic Catheter System and Methods", filed Dec. 8, 2006; U.S. patent application Ser. No. 11/637,951, entitled "Robotic Catheter System and Methods", filed Dec. 11, 2006; U.S. patent application Ser. No. 11/640,099, entitled "Robotic Catheter System and Methods", filed Dec. 14, 2006; U.S. Provisional Patent Application No. 60/879,911, entitled "Robotic Catheter System and Methods", filed Jan. 10, 2007; U.S. Provisional Patent Application No. 60/899,048, entitled "Robotic Catheter System and Methods", filed Feb. 1, 2007; U.S. Provisional Patent Application No. 60/900,584, entitled "Robotic Catheter System and Methods", filed Feb. 8, 2007; U.S. Provisional Patent Application No. 60/902,144, entitled "Flexible Catheter Instruments and Methods", filed Feb. 15, 2007; and U.S. patent application Ser. No. 11/678,016, entitled "Method of Sensing Forces on a Working Instrument", filed Feb. 22, 2007.

FIELD OF INVENTION

The invention relates generally to robotically controlled systems, such as telerobotic surgical systems, and more particularly, to flushing a catheter of a robotic surgical system to remove or purge gas or air bubbles from the catheter lumen.

BACKGROUND

Robotic interventional systems and devices are well suited for performing minimally invasive medical procedures as opposed to conventional techniques wherein the patient's body cavity is open to permit the surgeon's hands access to internal organs. Traditionally, surgery utilizing conventional procedures meant significant pain, long recovery times, lengthy work absences, and visible scarring. Advances in technology have lead to significant changes in the field of medical surgery such that less invasive surgical procedures, in particular, minimally invasive surgery (MIS), are increasingly popular. A "minimally invasive medical procedure" is generally a procedure that is performed by entering the body through the skin, a body cavity, or an anatomical opening utilizing small incisions rather than large open incisions in the body.

Various medical procedures are considered to be minimally invasive including, for example, mitral and tricuspid valve procedures, patent formen ovale, atrial septal defect surgery, colon and rectal surgery, laparoscopic appendectomy, laparoscopic esophagectomy, laparoscopic hysterectomies, carotid angioplasty, vertebroplasty, endoscopic sinus surgery, thoracic surgery, donor nephrectomy, hypodermic injection, air-pressure injection, subdermal implants, endoscopy, percutaneous surgery, laparoscopic surgery, arthroscopic surgery, cryosurgery, microsurgery, biopsies, videoscope procedures, keyhole surgery, endovascular surgery, coronary catheterization, permanent spinal and brain electrodes, stereotactic surgery, and radioactivity-based medical imaging methods. With MIS, it is possible to achieve less operative trauma for the patient, reduced hospitalization time, less pain and scarring, reduced incidence of complications related to surgical trauma, lower costs, and a speedier recovery.

Special medical equipment may be used to perform minimally invasive procedures. Typically, a surgeon inserts small tubes or ports into a patient and uses endoscopes or laparoscopes having a fiber optic camera, light source, or miniaturized surgical instruments. Without a traditional large and invasive incision, the surgeon is not able to see directly into the patient. Thus, the video camera serves as the surgeon's eyes. The images of the interior of the body are transmitted to an external video monitor to allow a surgeon to analyze the images, make a diagnosis, visually identify internal features, and perform surgical procedures based on the images presented on the monitor.

Minimally invasive procedures may involve minor surgery as well as more complex operations that involve robotic and computer technologies, which may be used during more complex surgical procedures and have led to improved visual magnification, electromechanical stabilization, and reduced number of incisions. The integration of robotic technologies with surgeon skill into surgical robotics enables surgeons to perform surgical procedures in new and more effective ways.

Although minimally invasive surgical techniques have advanced, physical limitations of certain types of medical equipment still have shortcomings and can be improved. For example, during a minimally invasive medical procedure, a guide catheter may be inserted into a body cavity duct or vessel. A catheter is an elongated tube that may, for example, allow for drainage or injection of fluids or provide a path for delivery of other working or surgical instruments, such as an ablation catheter, to a surgical or treatment site. During use, however, air bubbles may form within the catheter lumen before, during or after delivery of the working instrument, or during exchange of one working instrument for another working instrument, thereby resulting in bubbles being pushed into the patient, which can cause complications during surgery. There are known methods and devices for flushing catheters in an attempt to purge the catheter of air bubbles, but air bubbles may nevertheless form to complicate surgical procedures. Thus, the manner in which catheter lumens are flushed to remove bubbles can be improved.

SUMMARY

According to one embodiment, an apparatus or interface valve assembly for flushing a lumen of a catheter instrument comprises an interface valve and fluid supply and purge lines. The interface valve has a proximal end, a distal end and defines a lumen. The distal end is adapted for attachment to a proximal end of the catheter instrument, and the interface valve lumen is configured to receive a working instrument through the interface valve proximal end for insertion into the catheter instrument lumen. The fluid supply line is coupled to the interface valve and is in fluid communication with at least a portion of the interface valve lumen. First and second purge lines are also coupled to the interface valve. The first and second purge lines are controllable such that fluid (which may include liquid and gas such as bubbles) flowing into the interface valve lumen can be manipulated to flow in different directions through different portions of the interface valve lumen for evacuation through different purge lines.

According to another embodiment, a system for flushing a lumen of a catheter instrument of a robotic surgical system comprises a robotically controllable catheter instrument, a robotically controllable sheath instrument, a working instrument, an interface valve and fluid supply and purge lines. The catheter instrument is coaxially positioned within the sheath instrument. A distal end of the interface valve is adapted for attachment to a proximal end of the catheter instrument, and a lumen defined by the interface valve is configured to receive the working instrument through the interface valve proximal end for insertion into the catheter instrument lumen. The fluid supply and first and second purge lines are coupled to the interface valve. The fluid supply line is in fluid communication with at least a portion of the interface valve lumen. The purge lines are controllable such that fluid (which may include liquid and gas such as bubbles) flowing into the interface valve lumen can be manipulated to flow in different directions through different portions of the interface valve lumen for evacuation through different purge lines.

A further embodiment is directed to a method of flushing a lumen of a catheter instrument to remove air bubbles from the catheter instrument lumen. The method comprises introducing a fluid into a lumen of an interface valve that has a distal end adapted for attachment to a proximal end of the catheter instrument and defining a lumen configured to receive a working instrument through a proximal end of the interface valve for insertion into the catheter instrument lumen. The method further comprises controlling the purging of fluid (which may include liquid and gas such as bubbles) from the interface valve lumen such that fluid flowing into the interface valve lumen can be manipulated to flow in different directions through different portions of the interface valve lumen for evacuation through different purge lines.

Another embodiment is directed to an apparatus for sealingly engaging a working instrument configured for insertion into a robotically controllable guide catheter. The apparatus comprises a chamber body, a fastener and compliant spacer elements. The chamber body has a proximal end configured for receiving the working instrument and a distal end configured for interfacing with a proximal end of the guide catheter. The working instrument includes an elongate body that can be advanced through a lumen defined by the chamber body and into a lumen defined by the guide catheter. The fastener is coupled to the proximal end of the chamber body and configured to removably secure the working instrument within the chamber body lumen. The compliant spacer elements are positioned in the chamber body to provide a fluid tight seal along a portion of the elongate body of the working instrument located within the chamber body.

In one or more embodiments involving spacer elements, such as compliant washers, the spacer elements are configured to maintain the fluid tight seal while the working instrument is moved forwards and backwards within the chamber body lumen, e.g. during dithering of the working instrument. Such spacer elements may define apertures through which the elongate body of the working instrument can be advanced such that a fluid tight seal is formed between an inner surface of the compliant washer defining an aperture and an outer surface of the elongate body of the working instrument. A chamber body may also include dome seals that face different directions to seal different portions of the chamber body.

Further, in one or more embodiments, an outlet port is in fluid communication with the first and second purge lines such that fluid (e.g., liquid and/or air bubbles) evacuated through the purge lines are evacuated through the outlet port.

Additionally, in one or more embodiments, the purge lines are controllable such that fluids flowing into the interface valve lumen can be manipulated to flow in a forward direction towards the catheter instrument, or in a backwards direction away from the catheter instrument. This may be accomplished using clamps, e.g., pinch clamps, associated with or coupled to each purge line. In this manner, purge lines can be clamped to manipulate the direction of fluid flow, thereby manipulating the manner in which fluids flow through the interface valve lumen and through which purge tube the fluid is evacuated. For purposes of evacuation, the outlets of the purge tubes can be inputs to an adapter, the output of which is in fluid communication with an outlet or exhaust port to release or capture expelled materials. A one-way valve may be provided within the fluid path, e.g., between the adapter and outlet port, to ensure that fluid does not flow back into the catheter. Purge control elements in the form of clamps may be positioned between the adapter and the outlet port, and between the adapter and the interface valve.

In one or more embodiments, the interface valve comprises a bellows assembly that is in fluid communication with one of the purge lines. The bellows assembly includes first and second bellows members. The first member has a port extending there from, and the second member defines an aperture. The first and second bellows members are arranged such that the port and the aperture are in fluid communication with the purge line and gas and fluid flowing through the bellows assembly can be released through the aperture and the port and into the purge line.

In one or more embodiments, the interface valve comprises a valve assembly that is configured to close a portion of the interface valve lumen when the working instrument is not inserted through the valve assembly. Thus, fluid can flow into a first portion of the interface valve lumen, but not another portion. In one embodiment, in this configuration, fluid can flow into a first portion that is closer to the distal end of the interface valve, but does not flow in the opposite direction towards the proximal end of the interface valve. For example, in one embodiment, the valve assembly includes a valve or chamber body in fluid communication with a purge line, an interface, a seal and a fastener. The interface is configured to be secured to the valve body, and the seal is capable of assuming opened or closed states depending on compression of the seal member. More specifically, when uncompressed or relaxed, the seal member is opened to define an inner lumen or aperture that is sufficiently large to allow a working instrument, such as an ablation catheter, to pass through, but when compressed the aperture is closed. Selective compression of the seal member may be achieved by manipulating a fastener, which may be threadedly securable to the interface member such that the seal member disposed between the fastener and the threaded member is compressed or uncompressed as the fastener is tightened and loosened, thereby controllably or selectively closing or sealing the aperture or lumen through the interface valve (e.g., when no working instrument is inserted), or opening the aperture or lumen when a working instrument is to be inserted through the fastener and through the interface valve.

In one or more embodiments involving a fluid supply or inlet line and two purge or evacuation lines, the fluid supply line is coupled in fluid communication with the interface valve at a first location, a first purge line coupled in fluid communication with the interface valve at a second location, and a second purge line is coupled in fluid communication with the interface valve at a third location. The coupling points may be such that the first location is between the second and third locations, thus allowing fluids (e.g., liquid and gas such as bubbles) to flow in different directions through different portions of the interface valve lumen for evacuation through different purge lines.

BRIEF DESCRIPTION OF THE DRAWINGS

Referring now to the drawings in which like reference numbers represent corresponding parts throughout and in which:

FIG. 7K illustrates bellows assembly members that are separated from each other to illustrate fluid port and aperture components of bellows assembly members for releasing gas or bubbles;

DETAILED DESCRIPTION OF ILLUSTRATED EMBODIMENTS

Embodiments of the invention generally relate to apparatus, systems and methods for flushing a lumen of a catheter instrument to purge or remove gases or air bubbles from the catheter instrument lumen. Embodiments utilize a structural configuration that advantageously controls how flushing fluid flows through different purge lines using, e.g., pinch valves or other suitable controllers. In this manner, flow of fluids (e.g., liquid and gas such as bubbles) into and out of different sections of a lumen of an interface valve coupled to a proximal end of a catheter instrument and configured to receive a working instrument can be manipulated such that fluids flow in different directions through different portions of the interface valve lumen for evacuation of fluids through different purge lines. For example, purge tubes can be controlled to implemented a forward flush and/or a backwards flush and can be implemented before or during a surgical procedure, e.g., during an exchange of a working instrument. Robotic surgical systems in which embodiments of the invention may be implemented are described with reference to FIGS. 1-5B. Apparatus, system and method embodiments for removing or purging air bubbles from a catheter are described with reference to FIGS. 6A-8H.

Figure 1:
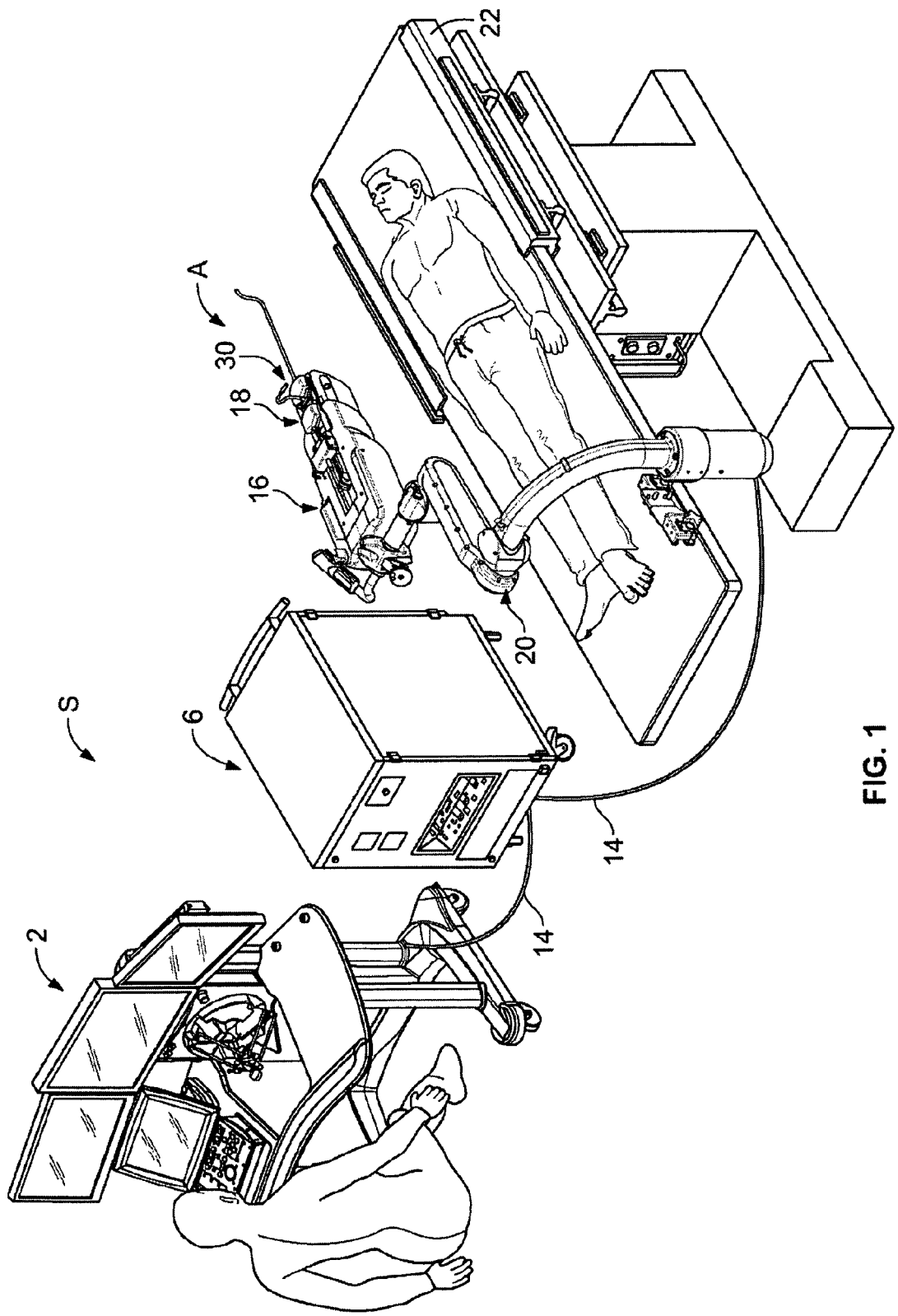
FIG. 1 illustrates a robotic catheter system in which apparatus, system and method embodiments for flushing a catheter lumen may be implemented.

Referring to FIG. 1, a robotically controlled surgical system (S) in which apparatus, system and method embodiments for flushing a central lumen of a catheter instrument (16) may be implemented includes a robotic catheter assembly (A) having a robotic sheath instrument (30) (generally referred to as "sheath instrument") and/or robotic catheter or guide or catheter instrument (18) (generally referred to as "catheter instrument") that are controllable using a robotic instrument driver (16). During use, a patient is positioned on an operating table (22) to which a robotic catheter assembly (A) is coupled or mounted. In the illustrated example, the system (S) includes an operator workstation (2), an electronics rack (6) and associated bedside electronics box, a setup joint mounting brace (20), and the instrument driver (16). A surgeon is seated at the operator workstation (2) and can monitor the surgical procedure, patient vitals, and control one or more catheter devices.

Various system (S) components in which embodiments of the invention may be implemented are illustrated in close proximity to each other in FIG. 1, but embodiments may also be implemented in systems (S) in which components are separated from each other, e.g., located in separate rooms. For example, the instrument driver (16), operating table (22), and bedside electronics box may be located in the surgical area with the patient, and the operator workstation (2) and the electronics rack (6) may be located, e.g., outside of the surgical area behind a shielded partition. System (S) components may also communicate with other system (S) components via a network to allow for remote surgical procedures during which the surgeon may be located at a different location, e.g., in a different building or at a different hospital utilizing a communication link transfers signals between the operator control station (2) and the instrument driver (16). System (S) components may also be coupled together via a plurality of cables or other suitable connectors (14) to provide for data communication, or one or more components may be equipped with wireless communication components to reduce or eliminate cables (14). In this manner, a surgeon or other operator may control a surgical instrument while being located away from or remotely from radiation sources, thereby decreasing radiation dosage to the operator.

Figure 2:
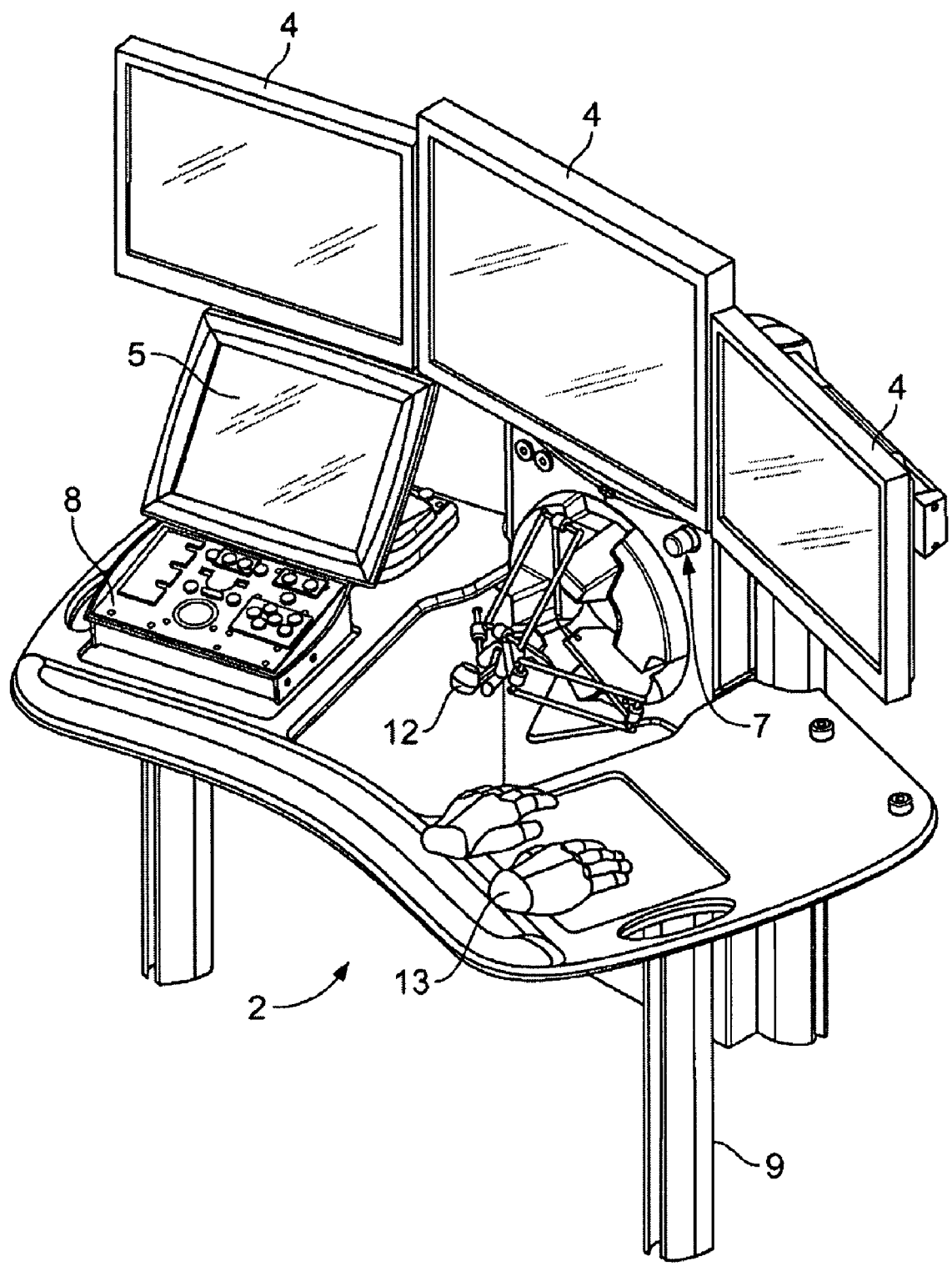
FIG. 2 illustrates an example of an operator workstation of a robotic catheter system with which control of a catheter can be inputted using different user interfaces and controls.

Referring to FIG. 2, one example of an operator workstation (2) that may be used with the system (S) shown in FIG. 1 includes three display screens (4), a touch screen user interface (5), a control button console or pendant (8), and a master input device (MID) (12). The MID (12) and data gloves (13) serve as user interfaces through which the surgeon can control operation of the instrument driver (16) and attached instruments. By manipulating the pendant (8) and the MID (12), a surgeon or other operator can cause the instrument driver (16) to remotely control a catheter instrument (18) and/or a sheath instrument (30) mounted thereon. A switch (7) may be provided to disable activity of an instrument temporarily. The console (9) in the illustrated system (S) may also be configurable to meet individual user preferences. For example, in the illustrated example, the pendant (8) and the touchscreen (5) are shown on the left side of the console (9), but they may also be relocated to the right side of the console (9). Further, optional keyboard may be connected to the console (9) for inputting user data. The workstation (2) may also be mounted on a set of casters or wheels to allow easy movement of the workstation (2) from one location to another, e.g., within the operating room or catheter laboratory. Further aspects of examples of suitable MID (12), data glove (13), and workstation (2) arrangements are described in further detail in U.S. patent application Ser. No. 11/481,433 and U.S. Provisional Patent Application No. 60/840,331, the contents of which were previously incorporated herein by reference.

Figure 3A:
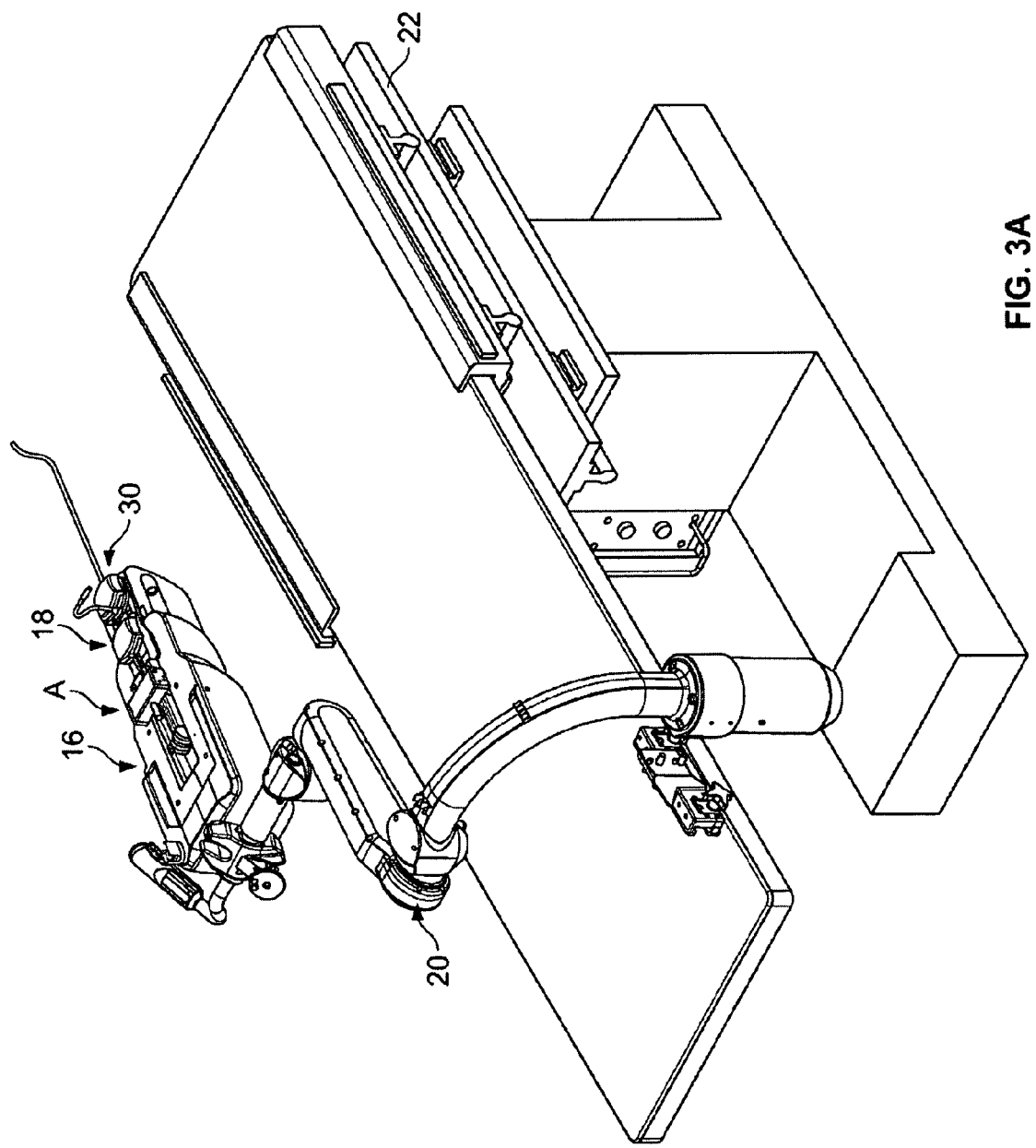
FIG. 3A illustrates an instrument driver mounting brace or a setup joint for supporting an instrument driver above an operating table.
Figure 3B:
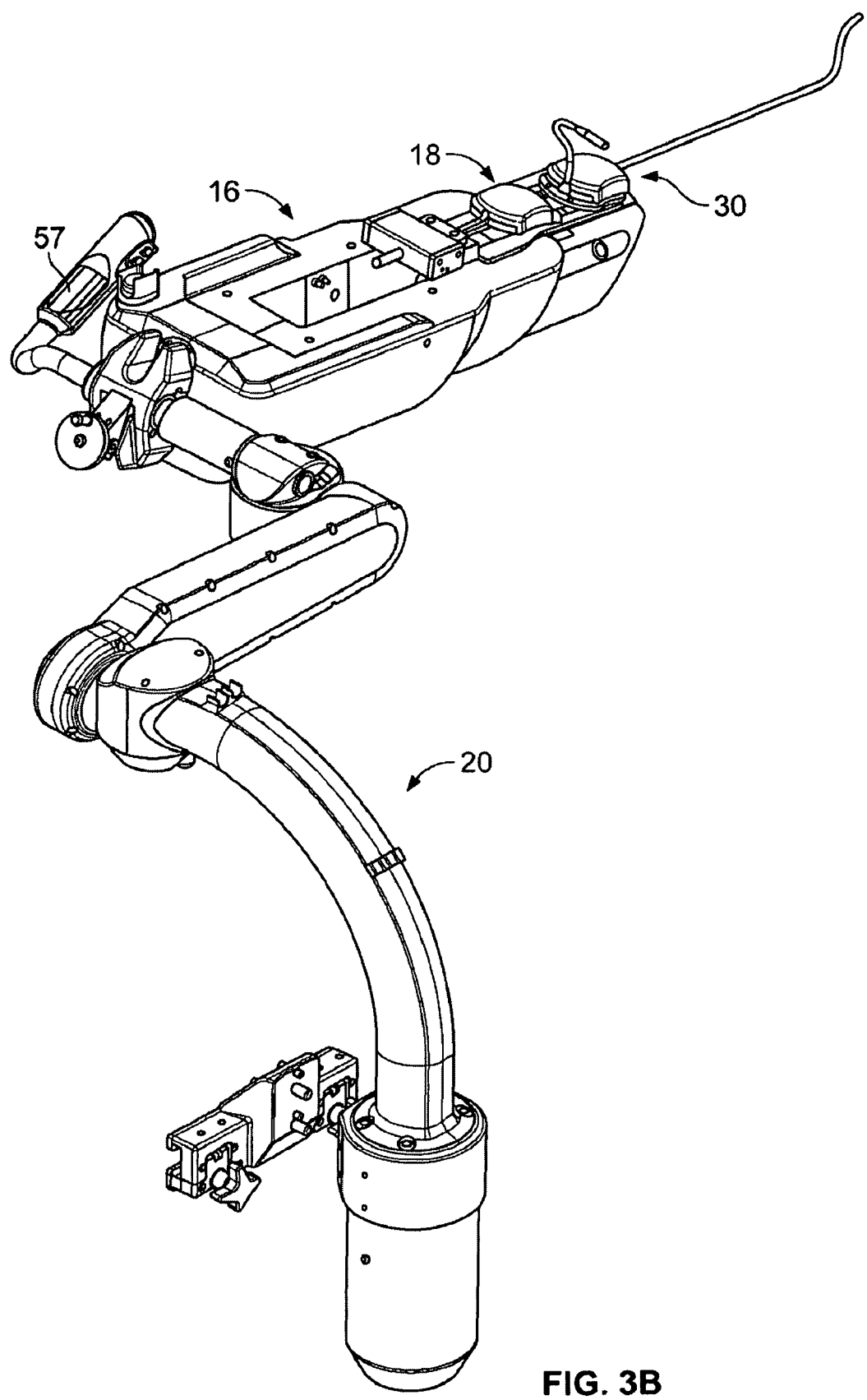
FIG. 3B is a rear perspective view of a support assembly or setup joint having an instrument driver mounted thereon.
Figure 3C:
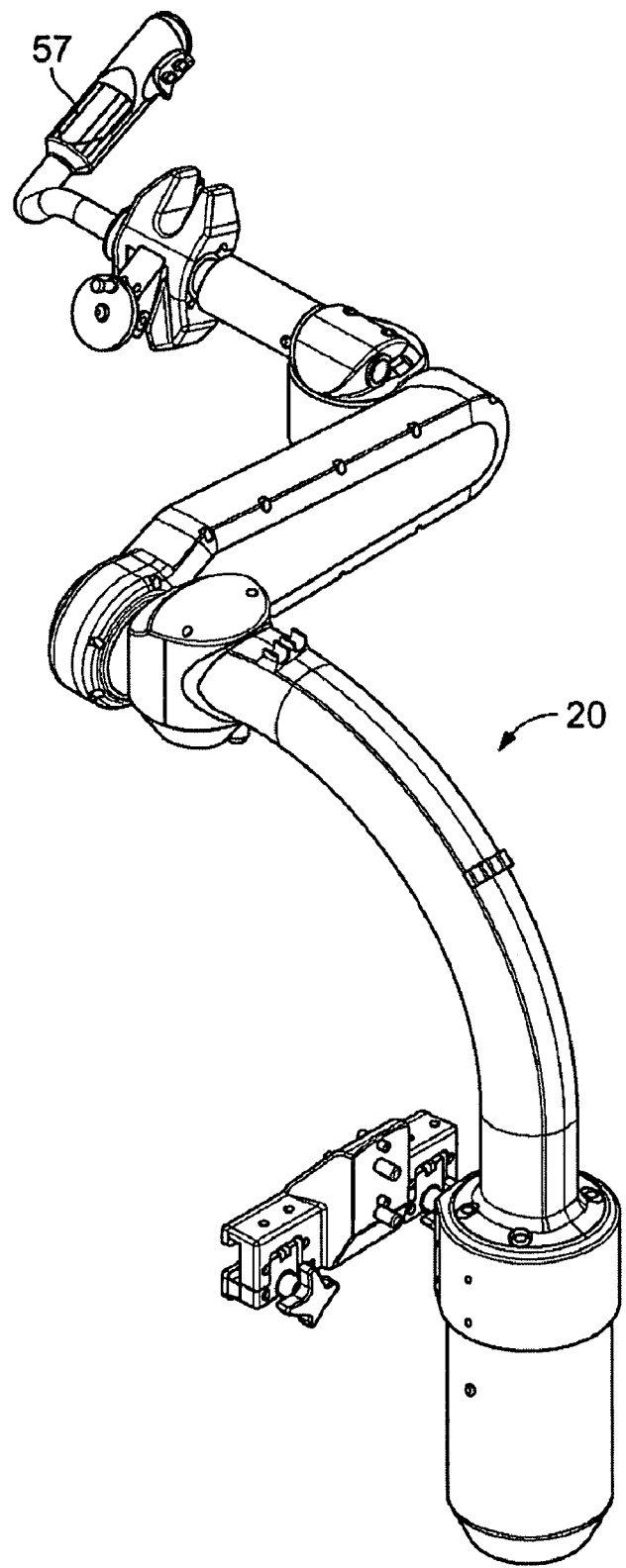
FIG. 3C illustrates a mounting brace or setup joint without the instrument driver.

Referring to FIGS. 3A-C, a system (S) includes a setup joint or support assembly (20) (generally referred to as "support assembly") for supporting or carrying the instrument driver (16) over the operating table (22). One suitable support assembly (20) has an arcuate shape and is configured to position the instrument driver (16) above a patient lying on the table (22). The support assembly (20) may be configured to movably support the instrument driver (16) above the operating table (22) in order to position the instrument driver (16) and allow convenient access to a desired location relative to the patient. The support assembly (20) may also be configured to lock the instrument driver (16) into a certain position.

In the illustrated example, the support assembly (20) is mounted to an edge of the operating table (22) such that a catheter and sheath instruments (18, 30) mounted on the instrument driver (16) can be positioned for insertion into a patient. The instrument driver (16) is controllable to maneuver the catheter and/or sheath instruments (18, 30) within the patient during a surgical procedure. Although the figures illustrate a single guide catheter (18) and sheath assembly (30) mounted on a single instrument driver (16), other system (S) configurations may be utilized. For example, embodiments may be implemented using a plurality of instrument drivers (16) on which a plurality of catheter/sheath instruments (18, 30) are controlled. Further aspects of a suitable support assembly (20) are described in U.S. patent application Ser. No. 11/481,433 and U.S. Provisional Patent Application No. 60/879,911, the contents of which were previously incorporated herein by reference.

Figure 4:
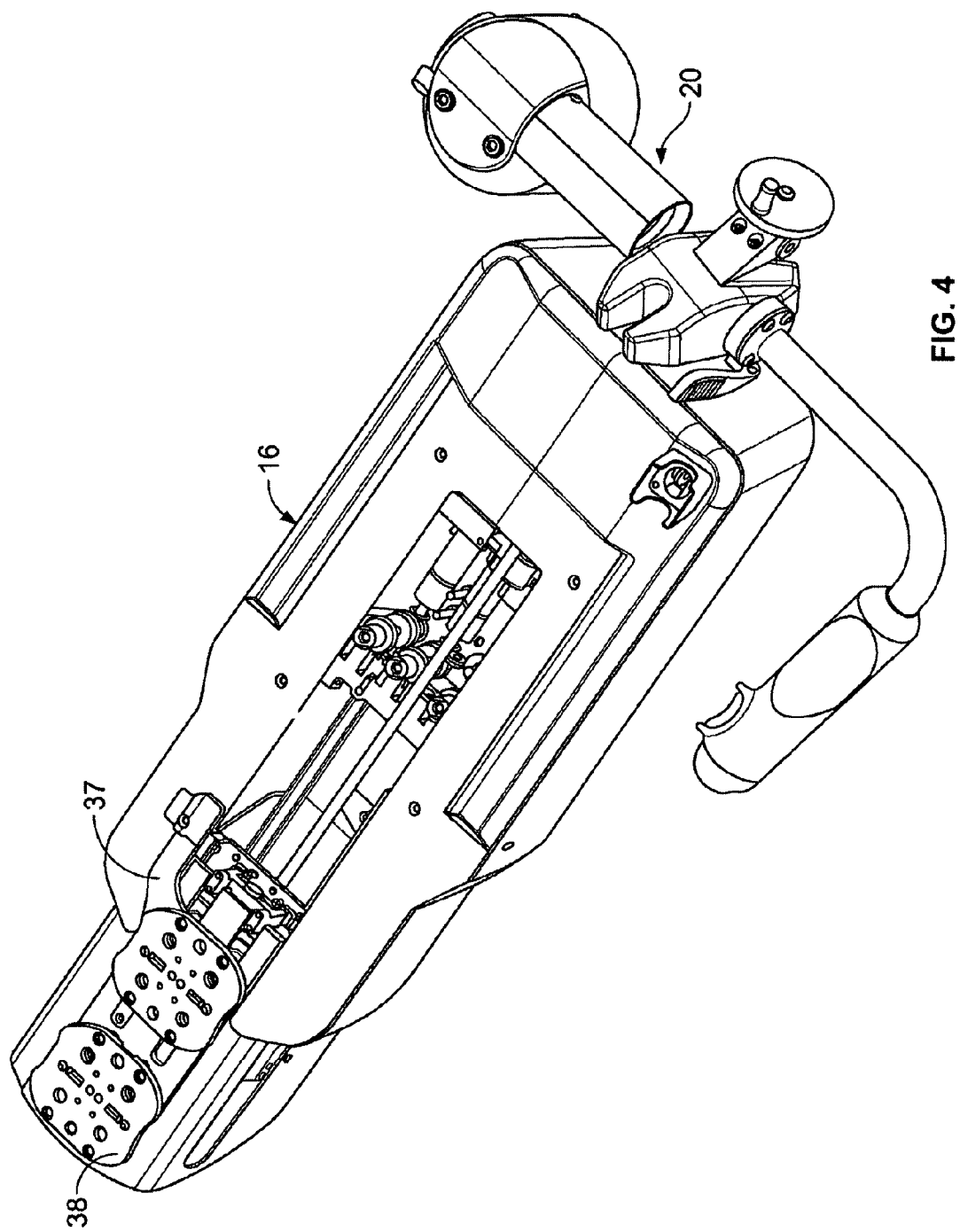
FIG. 4 illustrates an instrument driver mounted to a distal segment of a support assembly or setup joint.
Figure 5A:
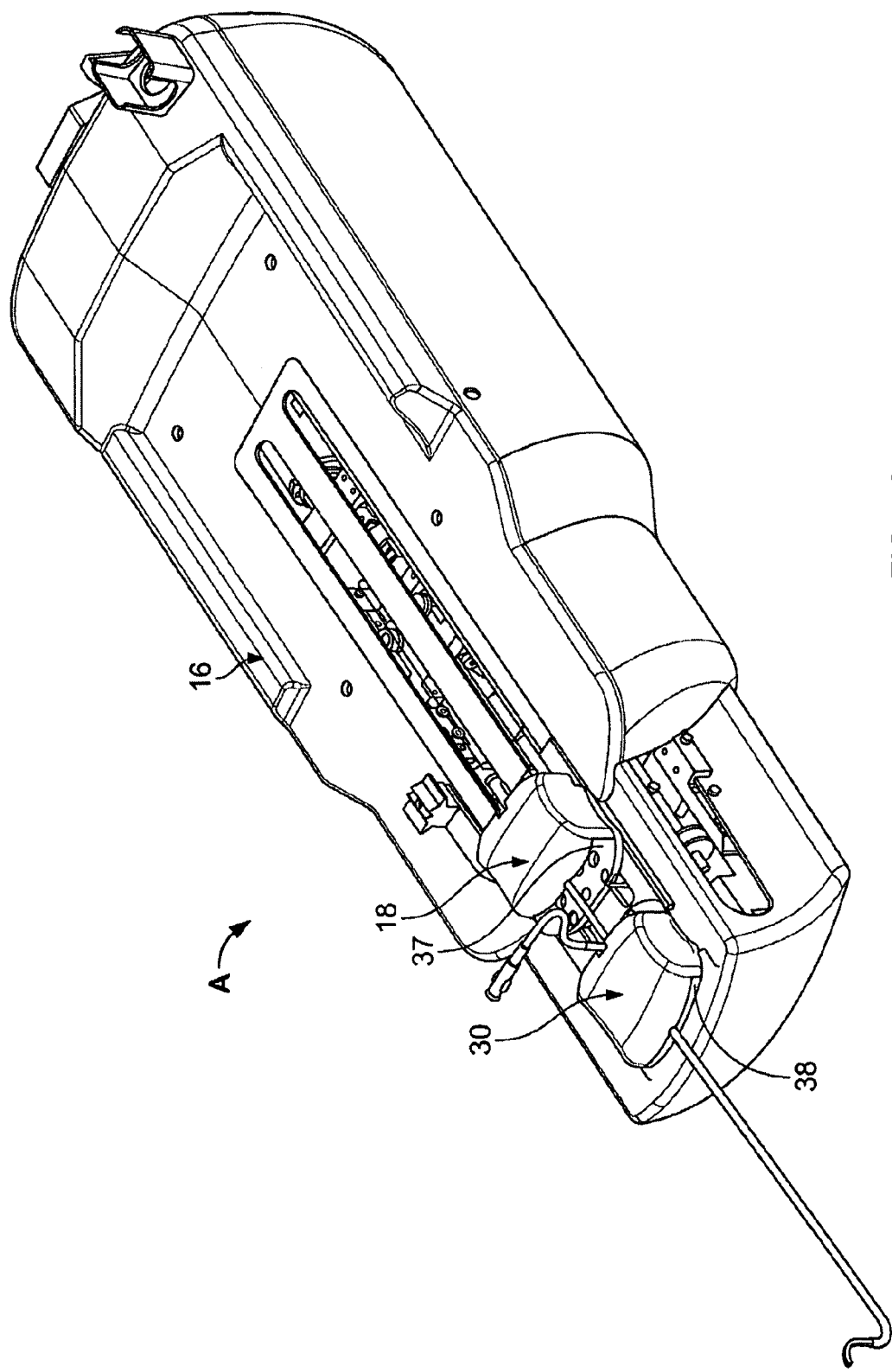
FIG. 5A illustrates a sheath and guide catheter assembly mounted on an instrument driver.
Figure 5B:
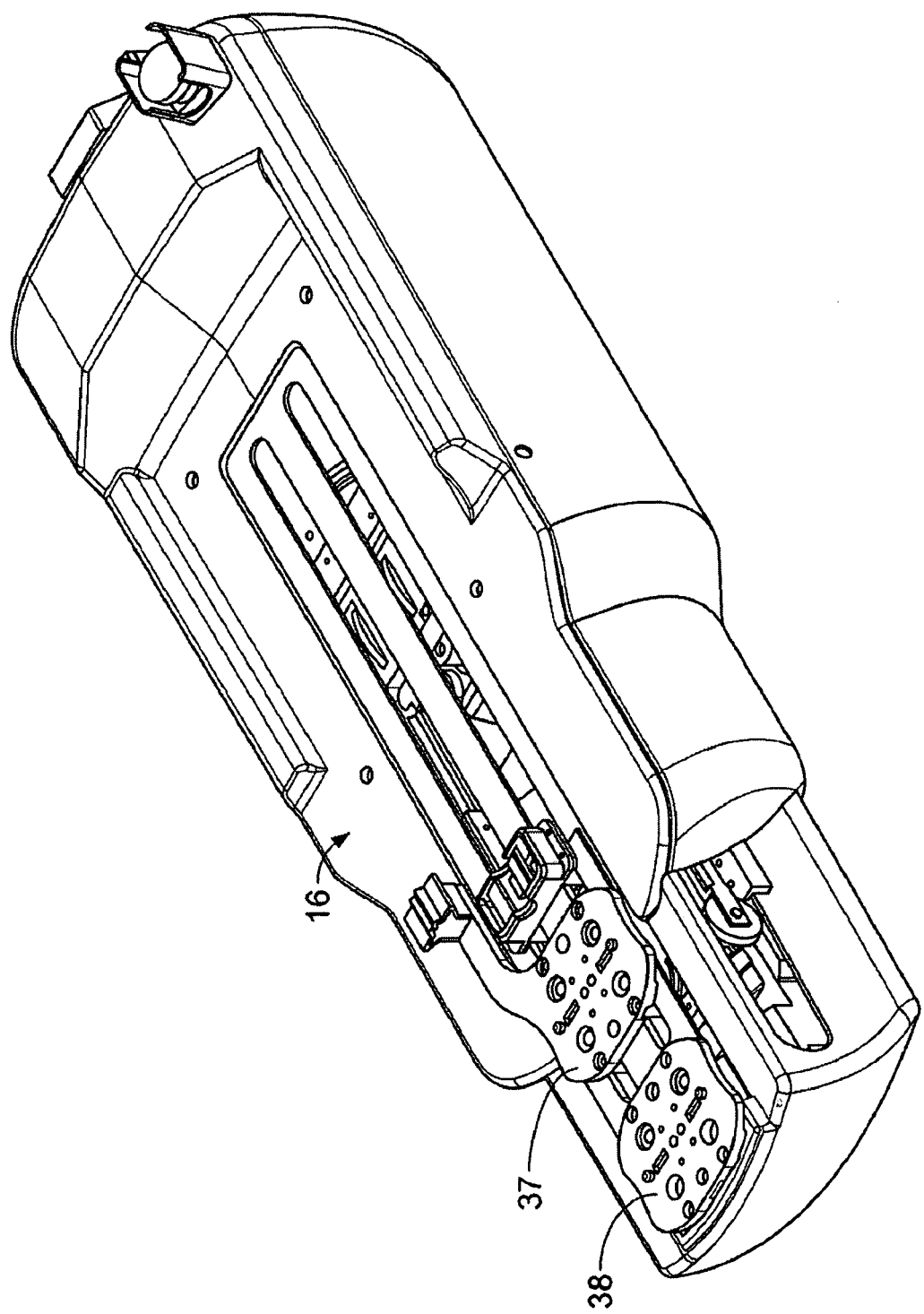
FIG. 5B further illustrates the instrument driver shown in FIG. 5A without the sheath and guide catheter assembly.

With further reference to FIGS. 4-5B, an instrument assembly (A) comprised of a sheath instrument (30) and an associated guide or catheter instrument (18) is mounted to associated mounting plates (37, 38) on a top portion of the instrument driver (16). FIGS. 5B-C further illustrate the instrument driver (16) in further detail without an attached instrument assembly. During use, the catheter instrument (18) is inserted within a central lumen of the sheath instrument (30) such that the instruments (18, 30) are arranged in a coaxial manner. Although the instruments (18, 30) are arranged coaxially, movement of each instrument (18, 30) can be controlled and manipulated independently. For this purpose, motors within the instrument driver (16) are controlled such that carriages coupled to the mounting plates (37, 38) are driven forwards and backwards on bearings. One or more components, such as the instrument driver (16), may also be rotated about a shaft to impart rotational motion to the catheter instrument (18) and/or sheath instrument (30). As a result, the guide catheter instrument (18) and the sheath instrument (30) can be controllably manipulated and inserted into and removed from the patient. Additional instrument driver (16) motors may be activated to control the bending of the guide catheter instrument (18) and the sheath instrument (30), the orientation of the distal tips of the instruments (18, 30), and any tools mounted at the distal tip of the catheter instrument (18).

Figure 6A:
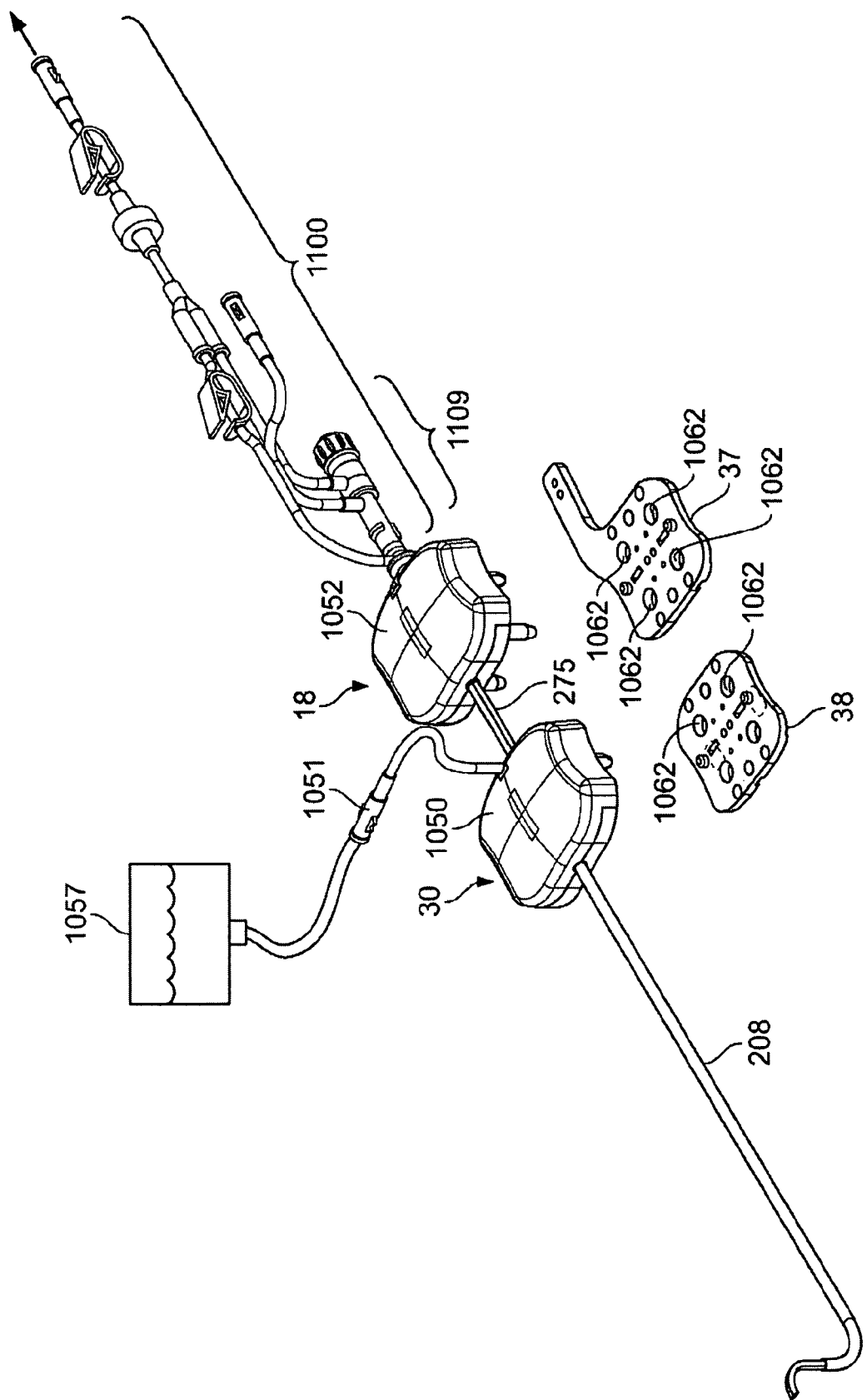
FIG. 6A illustrates a catheter flushing apparatus or interface valve assembly constructed according to one embodiment that includes an interface valve adapted for attachment to a proximal end of a catheter instrument or splayer.
Figure 6B:
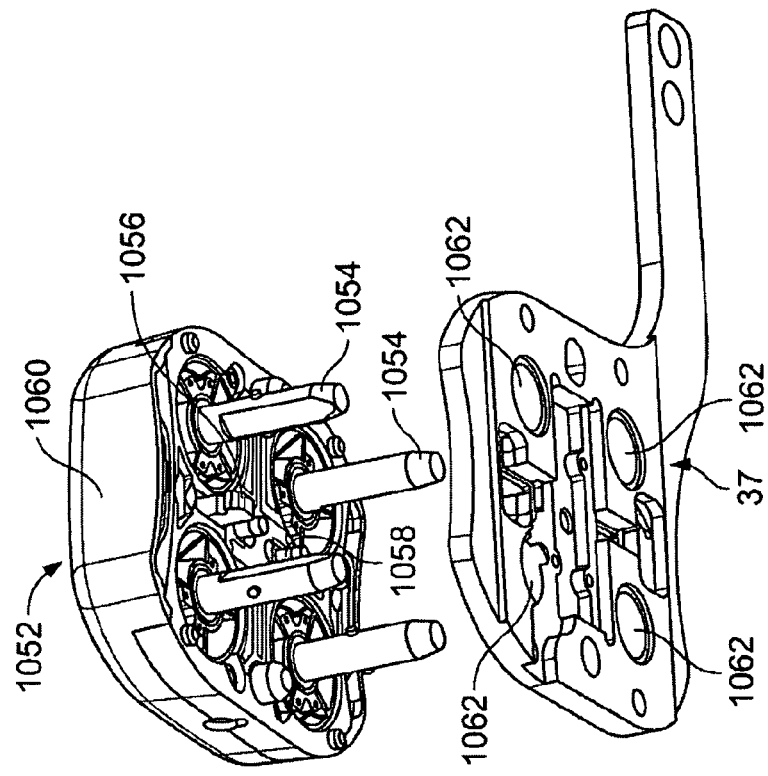
FIG. 6B illustrates sheath and guide splayers shown in FIG. 6A in further detail.
Figure 6B:
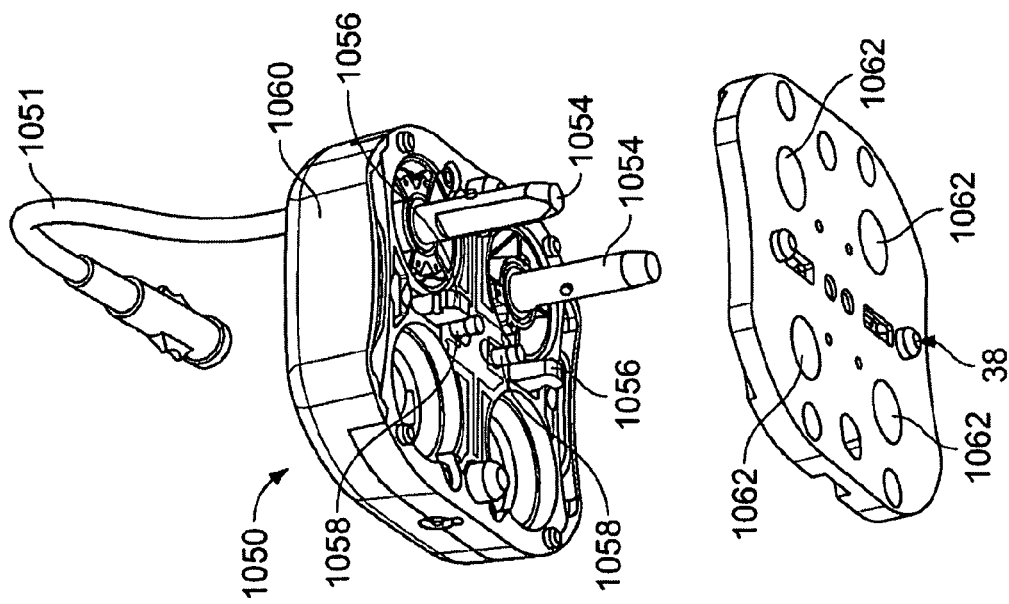

Referring to FIGS. 6A-B, apparatus and system embodiments directed to flushing a central lumen of a catheter instrument may include assembly (A) components as described above and an interface valve assembly (1100), which may be in the form of a Touhy assembly in one embodiment. FIG. 6A generally illustrates an interface valve assembly (1100) constructed according to one embodiment, and components of the interface valve assembly (1100) are described in further detail with reference to FIGS. 7A-L.

In the embodiment illustrated in FIGS. 6A-B, a sheath instrument (30) and a guide or catheter instrument (18) are positioned over their respective mounting plates (38, 37), and a guide catheter instrument member (275) that is coaxially interfaced with a sheath instrument member (208) as a result of the guide catheter instrument member (275) being inserted into a working lumen of the sheath catheter member (208). In the illustrated embodiment, the sheath instrument (30) and the guide or catheter instrument (18) are arranged in a coaxial manner, but the sheath instrument (30) may be used without a guide or catheter instrument (18), and a guide or catheter instrument (18) may be used without the sheath instrument (30). Thus, these instruments may also be mounted onto the instrument driver (16) individually.

The coaxial arrangement results in a guide catheter splayer (1052) that is located proximally relative to, or behind, the sheath splayer (1050) such that the guide catheter member (275) can be inserted into and removed from the sheath catheter member (208), and the interface valve (1100) is coupled to a proximal end of the catheter instrument (18) or guide catheter splayer (1052). According to one embodiment, the interface valve assembly (1000) is used to purge or remove gases or bubbles from a central lumen of the catheter instrument (18), and a flush port (1051) in fluid communication a fluid source (1057) (e.g., an IV bag or syringe) is used to flush fluid through the central lumen of the sheath instrument (30). The interface valve assembly (1000) and the flush port (1051) may use the same or different fluid source (1057). In this manner, multiple central lumens of different assembly (A) devices can be flushed and purged of gases and air bubbles to facilitate insertion of catheter and sheath instruments and working instruments into a patient.

FIG. 6B further illustrates sheath and guide splayers (1050, 1052) that are positioned for insertion into respective mounting plates (38, 37). When a catheter is prepared for use with an instrument, its splayer is mounted onto its appropriate interface plate. In this case, the sheath splayer (1050) is placed onto the sheath interface plate (38) and the guide splayer (1052) is place onto the guide interface plate (37). In one embodiment, both interface plates (37, 38) are located on the top surface of the instrument driver (16), and each interface plate (38, 37) includes four openings or apertures (1062) designed to receive corresponding drive shafts (1054), e.g., D-shaped, stainless steel insert molds or drive shafts. These drive shafts (1054) are attached to pulley assemblies of the splayers (1050, 1052).

In the illustrated embodiment, the two drive shafts (1054) of the sheath splayer (1050) are insertable within the right apertures or two openings (1062) of the sheath interface plate (38) as the splayer (1050) is mounted onto the instrument driver (16). Similarly, the four insert drive shafts (1054) of the guide splayer (1052) are insertable within the four apertures or openings (1062) of the guide interface plate (37). The sheath interface mounting plate (38) is similar to the guide interface mounting plate (37), and similar details are not repeated. Additional details regarding suitable splayers (1050, 1052) and related components are provided in, for example, U.S. Provisional Patent Application No. 60/801,355, the contents of which were previously incorporated herein by reference.

Referring again to FIG. 6A, and with further reference to FIGS. 7A-L, an apparatus or interface valve assembly (1000) for flushing a lumen of a guide catheter instrument (18) includes an interface valve or interface valve member (1109) (generally referred to as interface valve) having a distal end adapted for attachment to a proximal end of the catheter instrument (18) or splayer (1052) and a proximal end and lumen configured to receive a working instrument (generally illustrated as 1105), which is inserted through the interface valve (1100) and into the central lumen of the guide catheter instrument (18). The valve interface (1109) may be a haemostatic valve that is maintained under positive pressure and may be in the form of a Touhy interface. For ease of explanation, reference is made to an interface valve assembly or apparatus (1000) or an interface valve (1109).

Fluid from a fluid source (1057) (e.g., an IV bag or syringe), is delivered into the lumen of the interface valve (1100), and purge lines are independently controlled to manipulate the manner in which flushing fluid flows within the interface valve (1109) such that fluids (such as liquids and gas such as bubbles) may flow in different directions through different portions of the interface valve (1109) lumen for evacuation or extraction through different purge lines. In this manner, embodiments advantageously provide bi-directional flushing capabilities. Further, embodiments advantageously provide for flushing of different interface valve (1109) lumen sections. The manner in which the interface valve (1109) is constructed also facilitates maintaining of a sealed environment to reduce bubbles, even during manipulation of a working instrument (1105) that is inserted through the interface valve (1109). For example, the interface valve (1109) can maintain a sealed environment during dithering of an ablation catheter (1105) for use in determining contact forces between a distal end of the ablation catheter (1105) and tissue, as discussed in further detail below with reference to FIG. 7G.

Figure 7A:
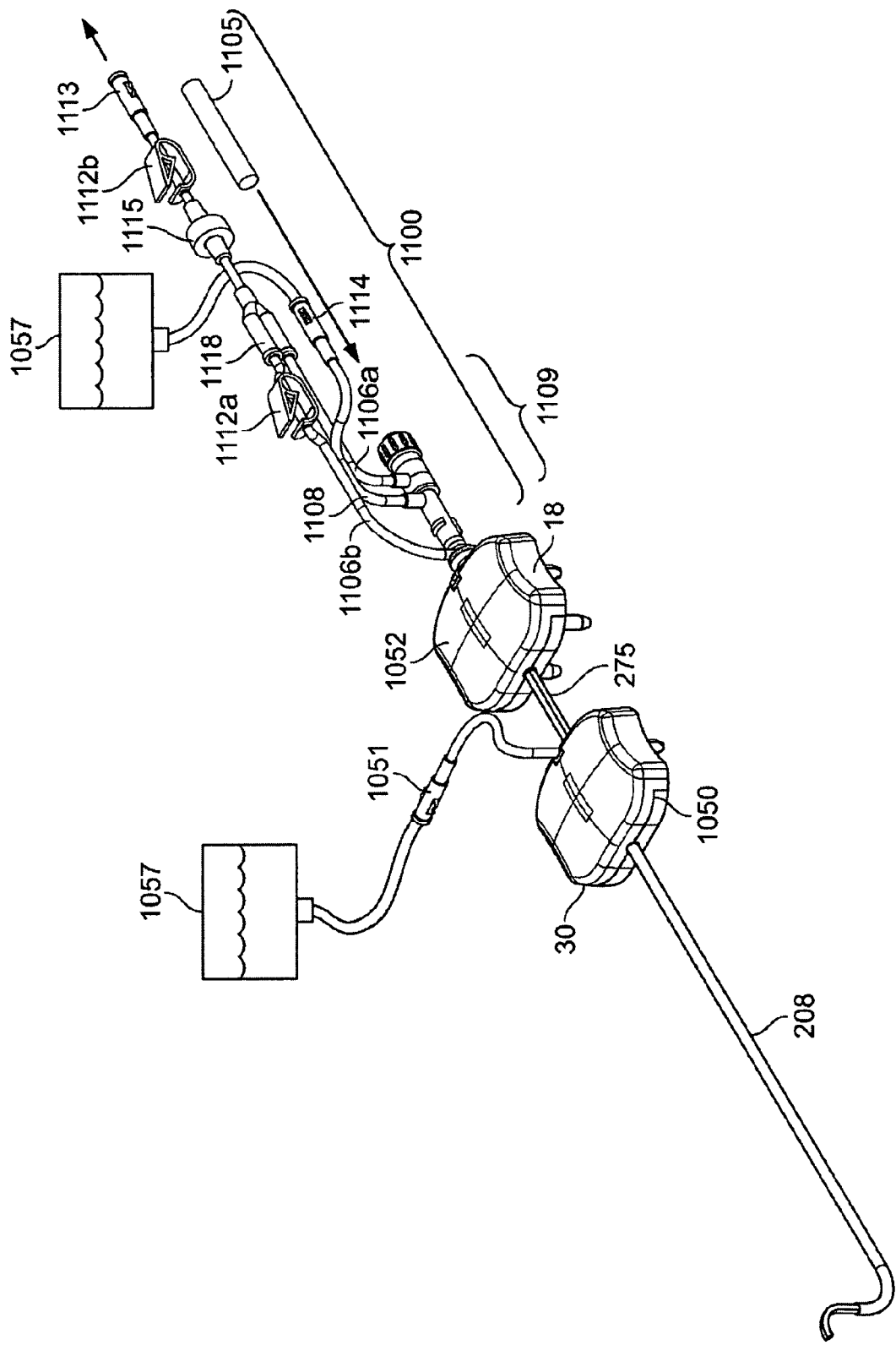
FIG. 7A illustrates a catheter flushing apparatus or interface valve assembly constructed according to one embodiment and the manner in which a working instrument is introduced into a catheter central lumen through a valve interface.
Figure 7B:
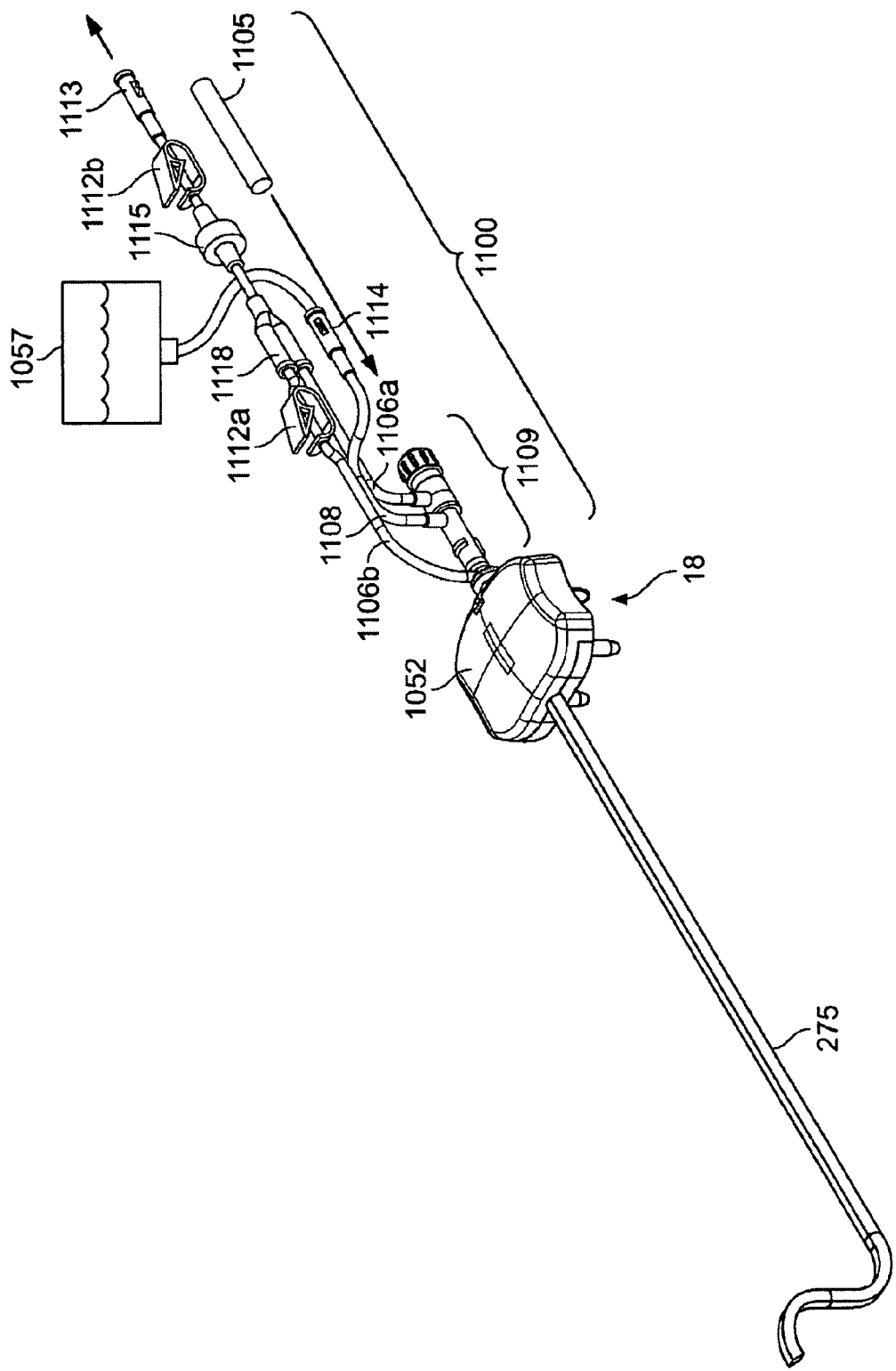
FIG. 7B further illustrates the catheter instrument splayer as shown in FIG. 7A.
Figure 7C:
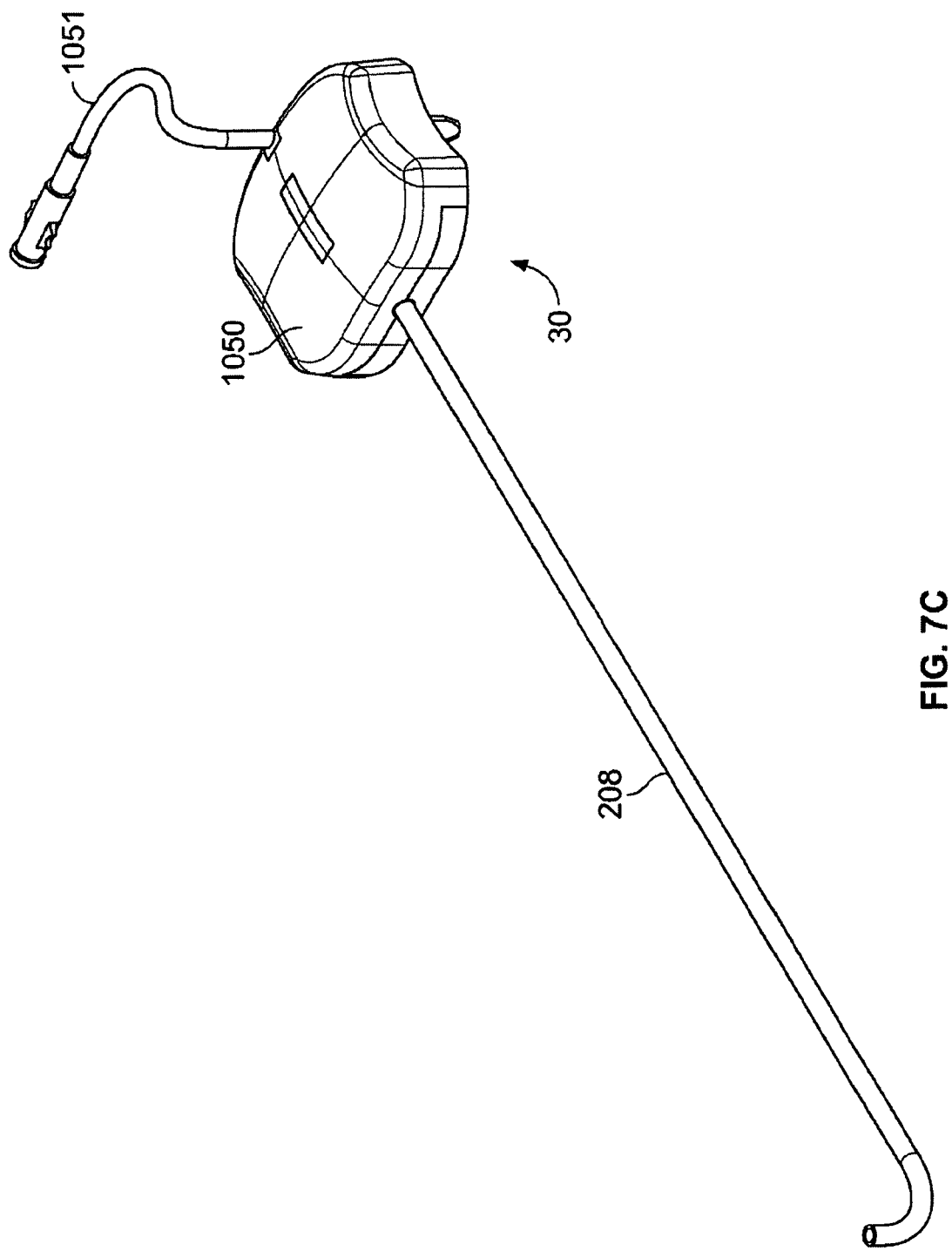
FIG. 7C further illustrates the sheath instrument splayer and associated fluid flush port as shown in FIG. 7A.
Figure 7D:
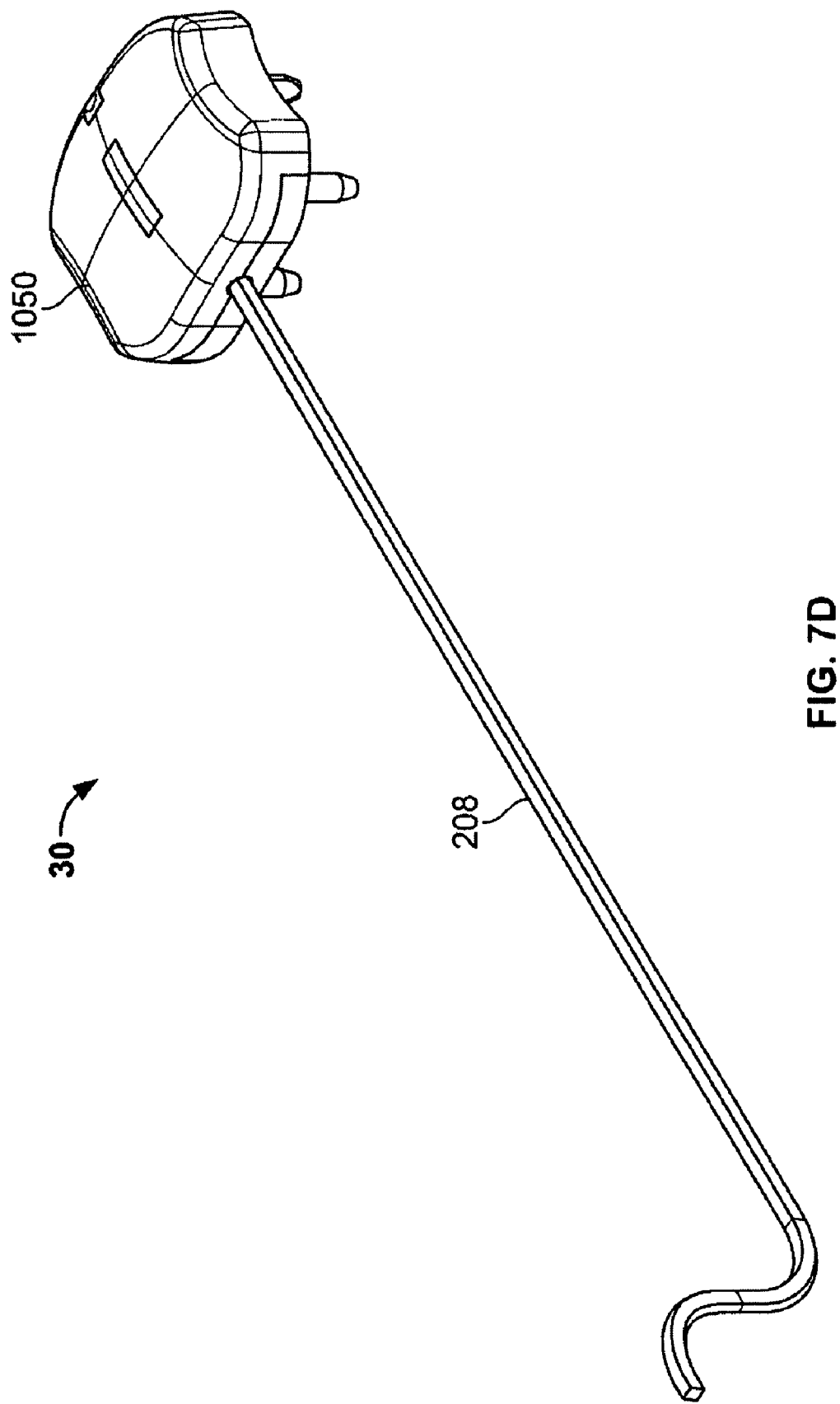
FIG. 7D further illustrates the sheath instrument splayer as shown in FIGS. 7A and 7C without the associated fluid port.
Figure 7E:
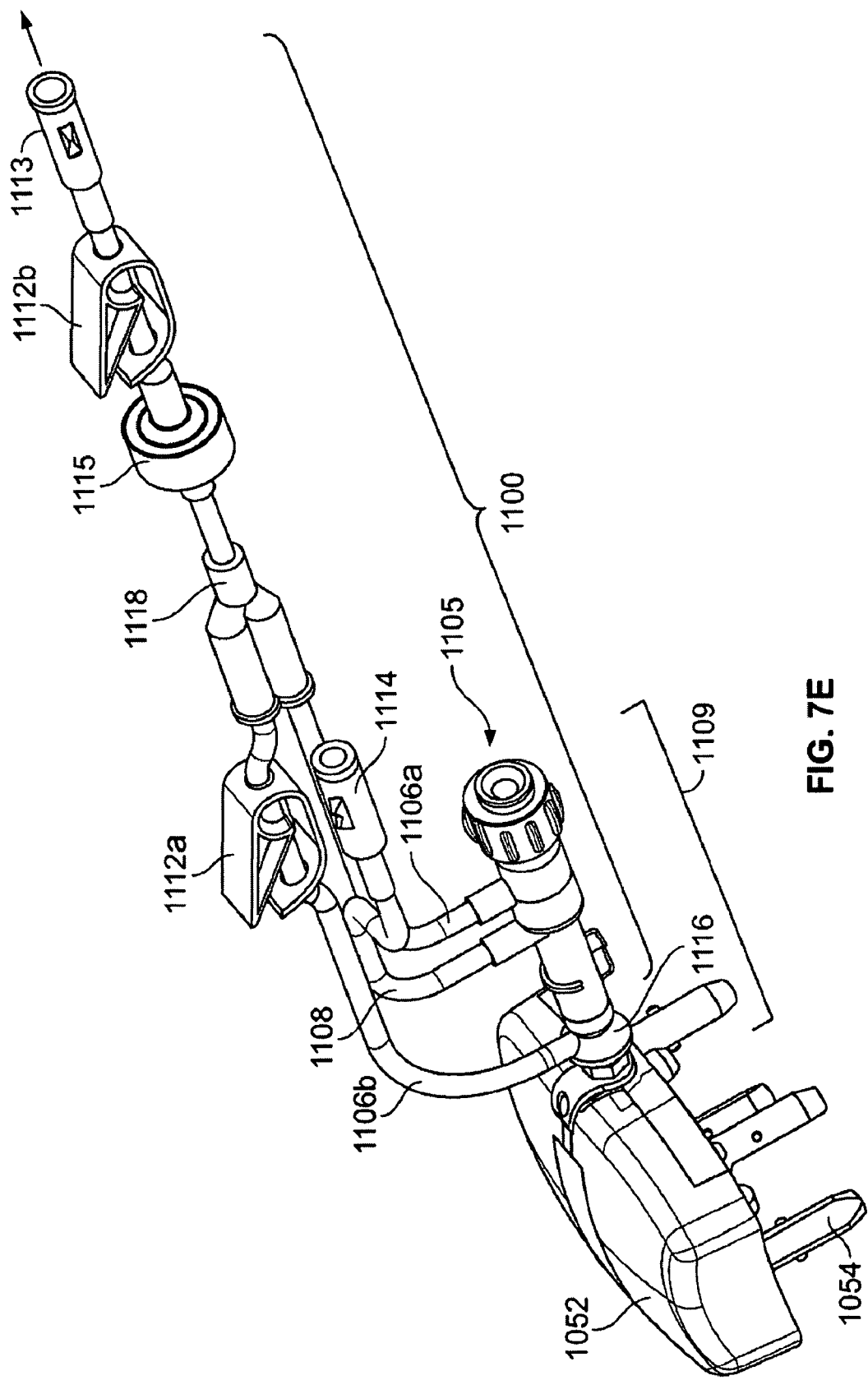
FIG. 7E is a perspective view of the apparatus or interface valve assembly shown in FIG. 7A and shows how the interface valve is coupled to a proximal end of a catheter instrument splayer.
Figure 7F:
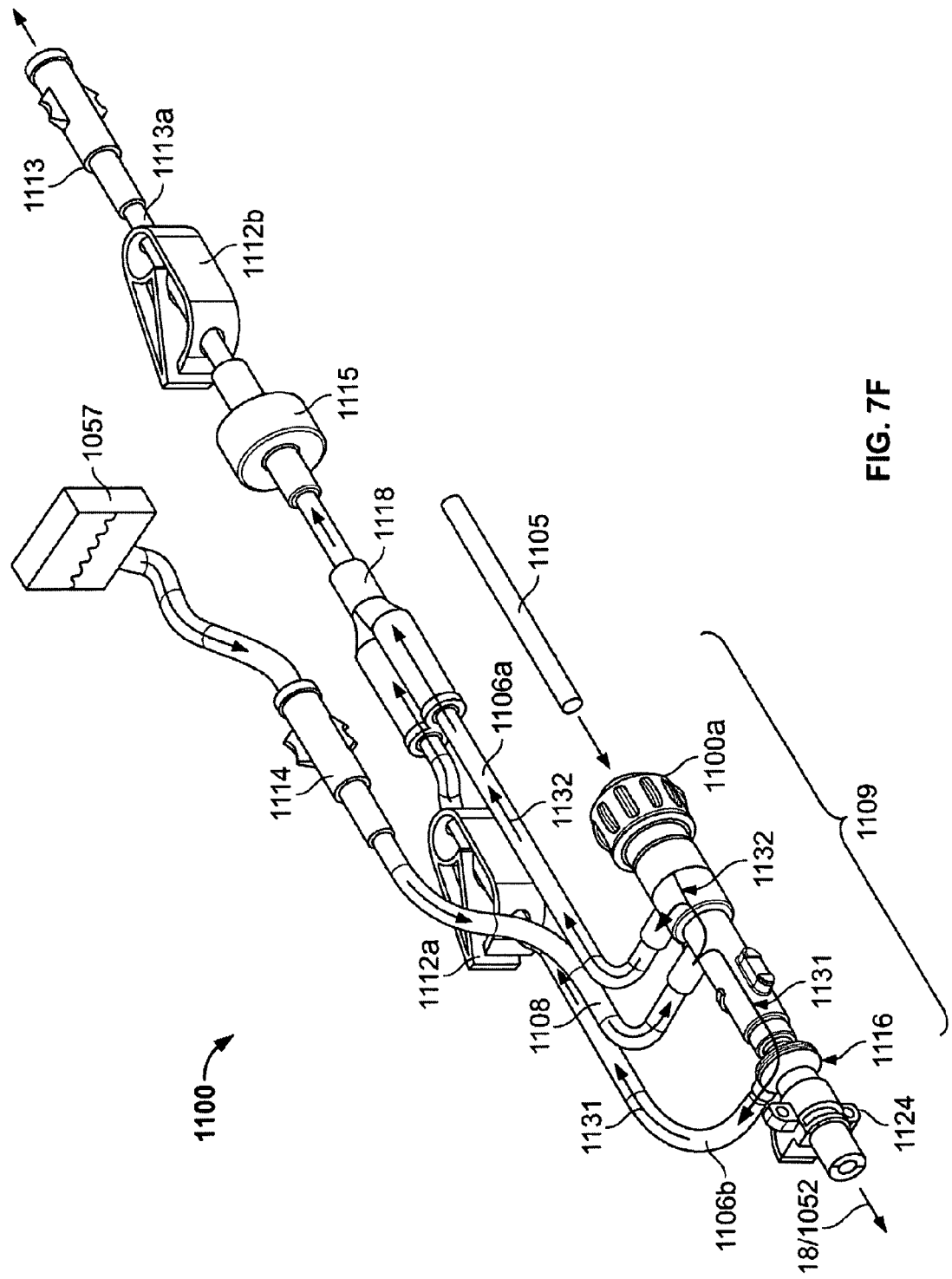
FIG. 7F is another perspective view of the apparatus or interface valve assembly shown in FIG. 7A and illustrates how bidirectional fluid flushes through different sections of the valve interface by control of different purge tubes can be implemented according to one embodiment.
Figure 7G:
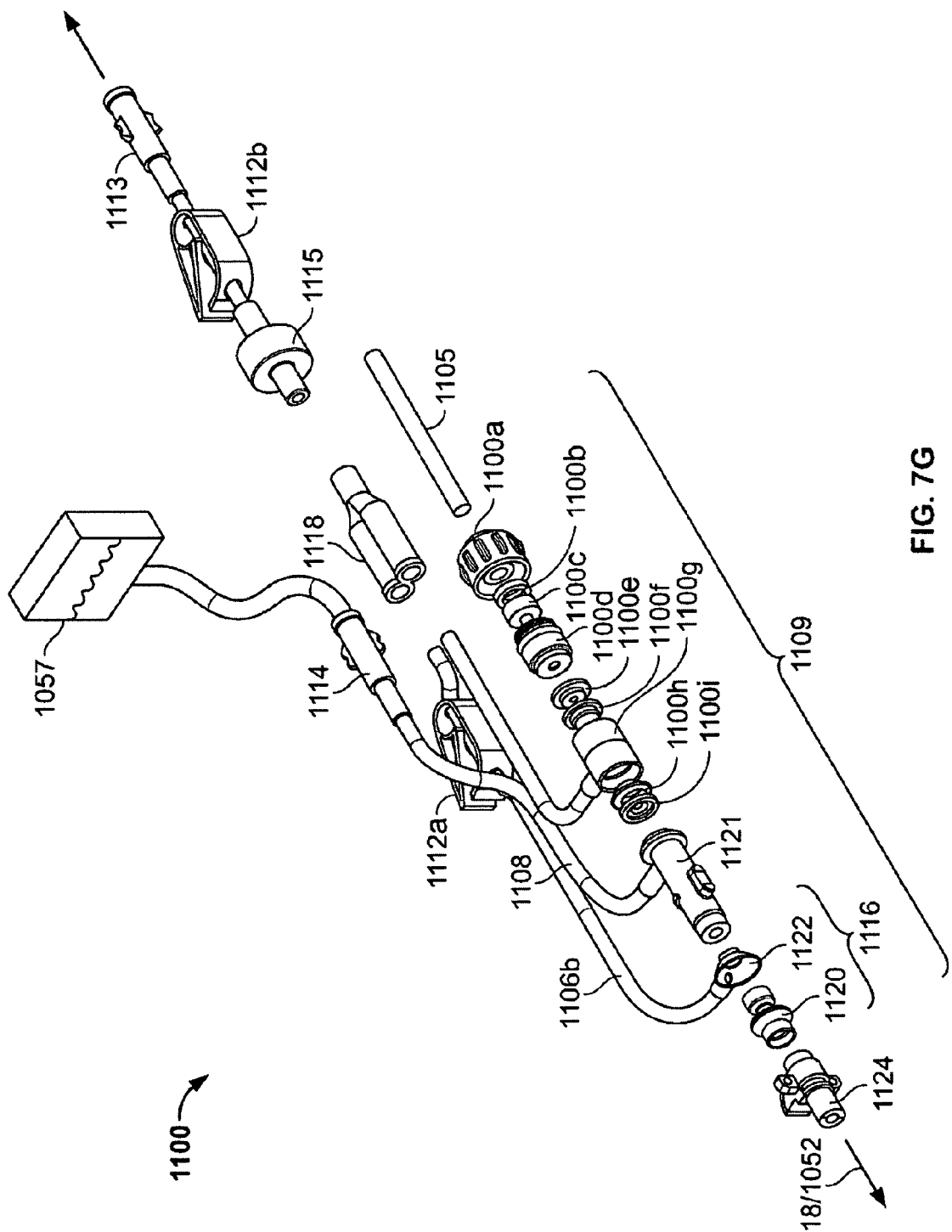
FIG. 7G is an exploded view of components of the interface valve.
Figure 7H:
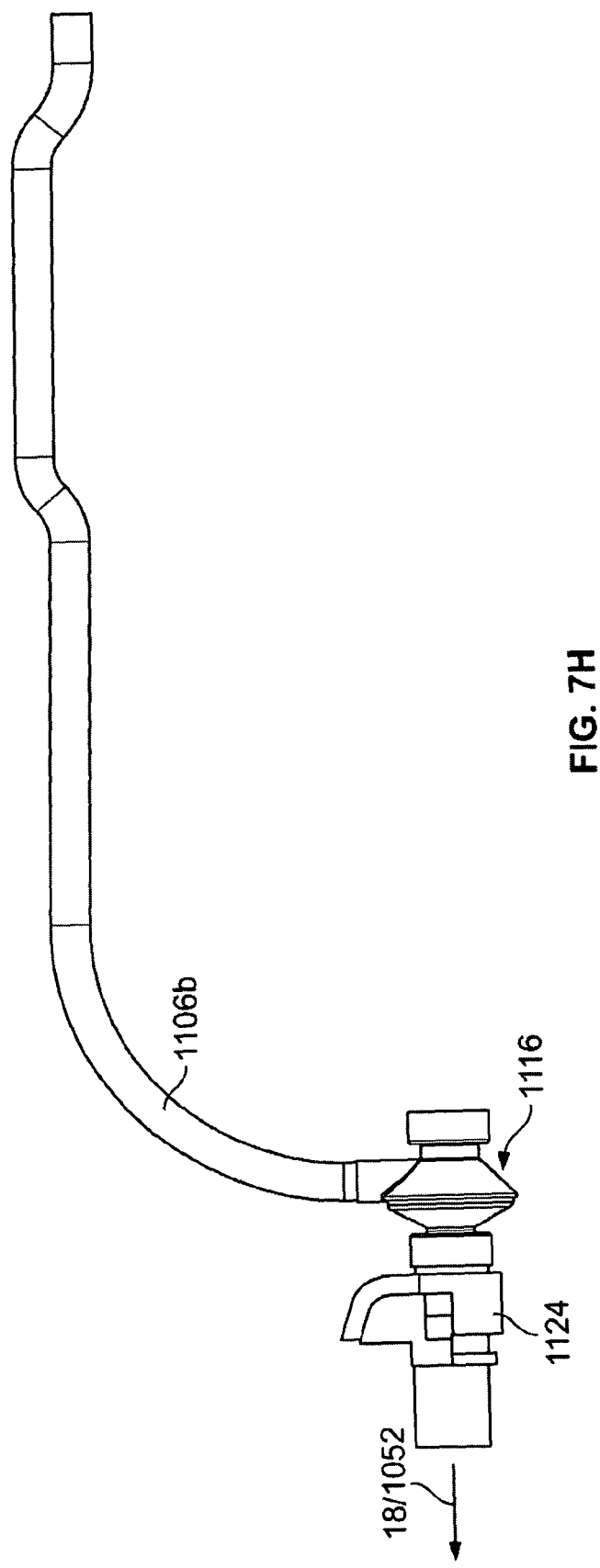
FIG. 7H further illustrates a purge tube in fluid communication with a bellows assembly that is coupled to a catheter splayer interface.
Figure 7I:
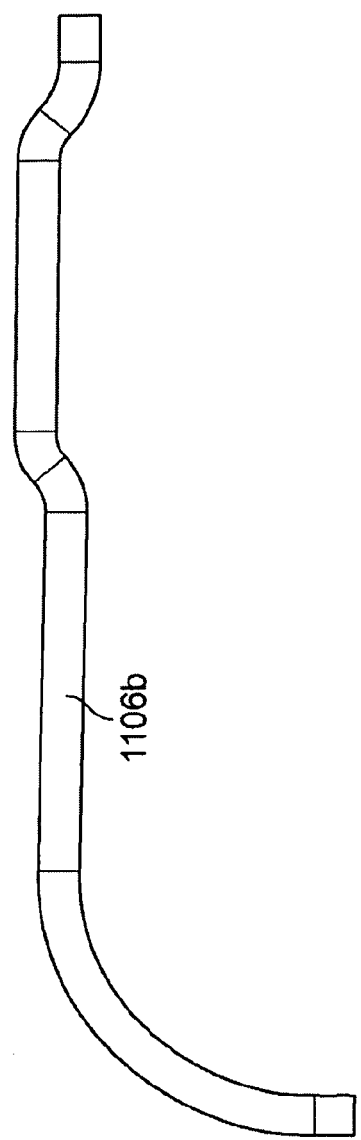
FIG. 7I illustrates the components shown in FIG. 7H separated from each other.
Figure 7I:
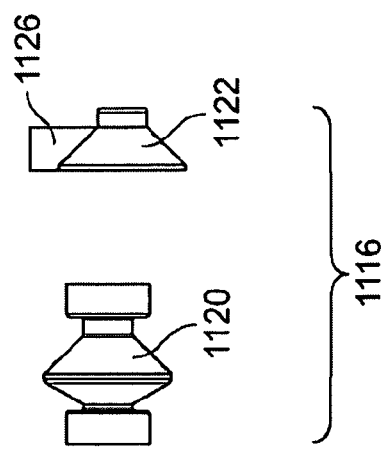
Figure 7J:
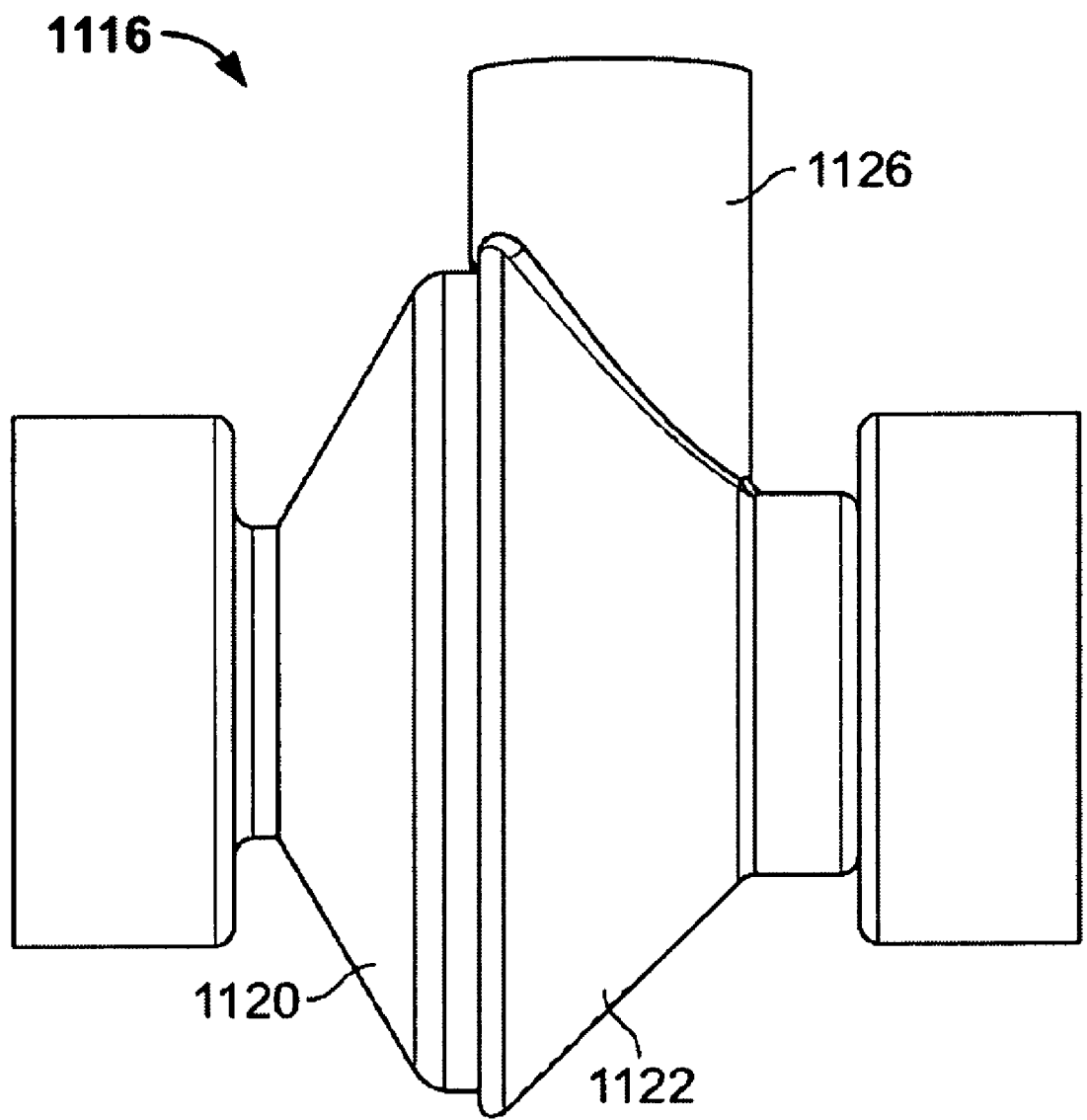
FIG. 7J illustrates a bellows assembly and bellows members that are attached to each other.

As shown in FIGS. 7A-G, and with particular reference to FIGS. 7E-G, an apparatus or interface valve assembly (1100) for flushing and purging or removing fluids (e.g. liquids and gas such as bubbles) (generally represented by flow arrows through inlet and purge lines) from a catheter instrument (18) of a robotic surgical system (S) includes an interface valve (1109), and which has a distal end coupled or attached to a proximal end of a catheter instrument (18) or associated splayer (1052) via a splayer adapter component (1124). In the illustrated embodiment, the interface valve assembly (1100) includes a fluid inlet tube (1108) in fluid communication with a fluid or flush port (1114), which is coupled to a fluid source (1057) (not shown in FIG. 7E) for providing flushing fluid to the interface valve (1109).

As shown in FIG. 7F, with multiple purge or evacuation lines (1106a,b) coupled to and in fluid communication with the interface valve (1109), there are multiple flush paths that may be used to flush different sections of the inner lumen of the interface valve (1109). In the illustrated embodiment, there is one fluid inlet tube (1108) and two purge lines (1106a, b), which are arranged such that flushing fluid flowing from the fluid source (1057) and through the fluid inlet port (1114) and the fluid inlet line (1108) may follow a first or forward flow path (1131) towards the catheter instrument (18) to perform a "forward" flush of a first section of the interface valve (1109) lumen. In an alternative embodiment, fluid may flow from the fluid source (1057) and through the fluid inlet port (114) and fluid inlet line (1108) to follow a second or backflow path (1132) away from the catheter instrument (18) to perform a "backwards" flush of a second, different section of the interface valve (1109) lumen. For this purpose, a flow restrictor (not shown) may be deployed at the distal end of the catheter instrument (18) to prevent fluid from flowing to the catheter distal tip initially. The flow restrictor is later removed at the end of the flow process before the catheter instrument (18) is introduced into the patient.

According to one embodiment, the interface valve assembly (1100) is configured such that fluid follows only one path (1131, 1132) at a given time. According to another embodiment, an interface valve assembly (1000) may be configured such that fluid follows both paths (1131, 1132) simultaneously. The flush path that is followed can be manipulated by controlling clamps on purge lines (1106a,b). Further, whether a single flush path (1131 or 1132) or multiple flush paths (1131 and 1132) are available may depend on, for example, various system parameters such as the pressure of the incoming fluid via the fluid line (1108), pressures within other lines, which purge lines are clamped, and the degree of clamping of the purge lines. For ease of explanation, reference is made to an interface valve assembly or apparatus (1000) that includes two purge lines (1106a,b) and that is configured such that fluid flows one flush path at a given time.

According to one embodiment, manipulation of flush paths and selection of the section of the interface valve (1009) lumen that is flushed is controlled using clamps (1112a,b) associated with or coupled to each purge line (1006a,b). For this purpose, the clamps (1112a,b) may be used to control stopcocks and according to one embodiment, the clamps (1112a,b) are pinch clamps.

In this embodiment, in order to achieve a forward flush of a first or downstream section of the interface valve (1109), the clamp (1112b) (otherwise referred to as a purge port pinch clamp) is closed to seal the purge line (1113a). As a result, flushing fluid does not flow through the purge line (1106a). When fluid is delivered into the interface valve (1109) lumen via fluid inlet tube (1108), the fluid follows the first flush path (1131) through a "downstream" section of the interface valve (1109) lumen, through a bellows assembly (1116), and into the distal purge line (1106b). The other clamp (1112a) (otherwise referred to as a bellows pinch clamp) is open to allow purged fluid to continue flowing through the purge line (1106b) and through an adapter (1118) which combines the purge lines (1106a,b) into a single purge line (1113a) via an adapter. Purged liquids and gas flow through the purge line (1113a) and through a one-way valve (1115) that may be used to prevent fluid flow back into the catheter instrument (18) lumen. The previously closed clamp (1112b) is opened (when necessary) to allow purged fluids to flow through the one-way valve (1115), through the unclamped purge line (1113a) to be released, expelled or extracted through outlet port (1113) and onto a drape or other element outside of the sterile field.

According to another embodiment, in order to achieve a reverse, backwards or backflow flush of a second, different section of the interface valve (1009) lumen, the clamp (1112a) is closed to seal the purge line (1106b). As a result, flushing fluid cannot flow through the purge line (1106b). Thus, when fluid is delivered into the interface valve (1109) lumen via fluid inlet tube (1108), the fluid follows the second flush path (1132) through a "backflow" section of the interface valve (1109) lumen, and into the purge line (1106a). The other clamp (1112b) is opened to allow fluid to continue flowing through the purge line (1106a), through the adapter (1118) and the one-way valve (1115) to be released, expelled or extracted through the outlet port (1113).

Although embodiments are described with reference to a single fluid inlet line (1108) and two purge lines (1106a,b) for bi-directional flushing of different sections of an interface valve (1109), other embodiments may involve other numbers of purge lines, which may be used to selectively flush different interface valve (1109) sections. Accordingly, Figures showing assemblies including two purge lines (1106a,b) and a single flush line (1108) are provided to illustrate one example of how embodiments may be implemented.

Further, although embodiments are generally described with reference to purging gas or bubbles from a central lumen for a working instrument (1105) such as an ablation catheter, it should be understood that embodiments may be implemented prior to insertion of the working instrument (1105) into the proximal end of the interface valve (1109), while the working instrument (1105) is positioned within the interface valve (1109) and within the central lumen of the catheter instrument (18), and after the working instrument (1105) has been removed, e.g., during a working instrument (1105) exchange. Thus, embodiments are adaptable to flush gases and bubbles at various stages of a surgical procedure as necessary.

FIG. 7G illustrates components of an interface valve assembly (1100) and interface valve (1109) constructed according to one embodiment in further detail for sealingly engaging an outer surface of a working instrument (1105), such as an elongate body or shaft of a working catheter, such as an ablation catheter. According to one embodiment, the interface valve (1109) includes a splayer adapter component (1124) for attachment to catheter splayer (1052), a mono bellows or bellows assembly (1116) that includes bellows members 1120 and 1122. Bellows member (1222) is a bellows purge port component that is in fluid communication with the purge line (1106b). The interface valve (1109) also includes a fluid interface member (1121), which is in fluid communication with fluid inlet line (1108) and inlet port (1114), and a plurality of interface valve components (1100a-i).

Components of an interface valve (1109) constructed according to one embodiment include a Touhy nut or other fastener (1100a), which defines a lumen for receiving a working instrument (1105), a washer (1100b), e.g., a nylon thrust washer, a compressible and resilient seal member (1100c), which is capable of closed or opened configurations in which an aperture or lumen is opened and defined through the seal member (1100c) depending on the compressive forces applied to the seal member (1100c), a threaded interface or connector (1100d), which has a threaded outer surface to threadedly engage a threaded inner surface of the fastener (1100a), a first washer seal (1100e), a first dome or backup seal (1100f), which prevents flow of fluid back into the central lumen of the catheter instrument (18), a valve or chamber body (1100g), which is in fluid communication with a purge line (1106b) and includes washer seal (1100e) and dome seal (1100f) and a second dome or backup seal (1100h) and a second washer seal (1100i).

The proximal end of the valve or chamber body (1100g) together with the dome seal (1100h) and washer seal (1100i) interface with a distal end of the fluid interface member (1121). The distal end of the valve or chamber body (1100g) together with the dome seal (1100f) and washer seal (1100e) interface with the threaded connector (1100d), which may be threadedly secured to the valve or chamber body (1100g). In the illustrated embodiment, the dome seals (1100f, 1100g) face different directions (e.g., forward and backwards directions) and one dome seal (1100f) is used to seal a proximal end of the valve or chamber body (1100g), and another dome seal (1100h) is used to seal a distal end of the valve or chamber body (1100g).

The distal end of the threaded connector (1100d) includes an outer threaded surface to threadedly engage an inner threaded surface of the fastener (1100a). With this configuration, when the fastener (1100a) is loose and not tightened against the connector (1100d), the intermediate seal member (1100c) is not compressed between the fastener (1100a)/washer (1100b) and connector (1100d). As a result, the seal member (1100c) assumes a relaxed or opened state, i.e., an aperture is formed through the seal member (1100c) to allow insertion of a working instrument (1105) through the fastener (1100a) and other interface valve (1109) components. When the fastener (1100a) is tightened against the connector (1100d), the intermediate seal member (1100c) is compressed between the fastener (1100a)/washer (1100b) and the connector (1100d), such that the seal member (1100c) is closed. Thus, rotation of the fastener (1100a) serves to controllably open or close an aperture or lumen through the seal member (1100c), thereby allowing or blocking access to the interface valve (1109) lumen to allow or disallow insertion of a working instrument (1105) through the interface valve (1109) and into the central lumen of the catheter instrument (18).

This interface valve (1109) provides a number of advantages. For example, the arrangement of connectors and sealing members provides a seal at multiple locations within the interface valve (1109) to prevent or reduce introduction of bubbles into the central lumen of the catheter instrument (18), which may result from inserting or withdrawing the working instrument (1105) from the interface valve (1109). Further, when the fastener (1100a) is tightened to compress and open the seal member (1100c) to allow insertion of a working instrument (1105), the inner surface of the seal member (1100c) that defines the aperture clamps around the outer surface of the working instrument (1105) to prevent or reduce movement or slipping of the working instrument (1105). This provides for more accurate control over the working instrument (1105). Additionally, in cases in which the working instrument (1105) is an ablation catheter, the interface valve (1109) configuration accommodates dithering of the ablation catheter (1105) while reducing or eliminating bubbles introduced into the catheter instrument (18) lumen. More particularly, the ablation catheter (1105) may be controllably vibrated or dithered for purposes of measuring the force on the distal tip of the ablation catheter (1105) as the ablation catheter (1105) is pushed against tissue. The combination of the valve body (1100g), threaded connector (1100d) and associated washers (1100e,i) and dome seals (1100f,h) allows dithering to be performed while seal integrity around the ablation catheter is maintained, thereby preventing or reducing introduction of any bubbles that may be formed into the catheter instrument (18) central lumen and into the patient. Thus, in addition to advantageously providing bi-directional flushing capabilities and flushing of selected sections of the interface valve (1109) lumen, embodiments also provide other important advantages.

Referring to FIG. 7G, and with further reference to Fig. H-L, embodiments of an interface valve (1109) includes a bellows assembly (1116) that is in fluid communication with one of the purge lines (1106b) and includes a first bellows member (1122) having a port (1126) extending there from and a second bellows member (1120) defining an aperture (1127). The dedicated purge port (1126) allows for extraction of air from the bellows without having to manually compress the bellows section numerous times or to increase the flush flow rate. The bellows members may, for example, be made by an injection molding process.

Figure 7L:
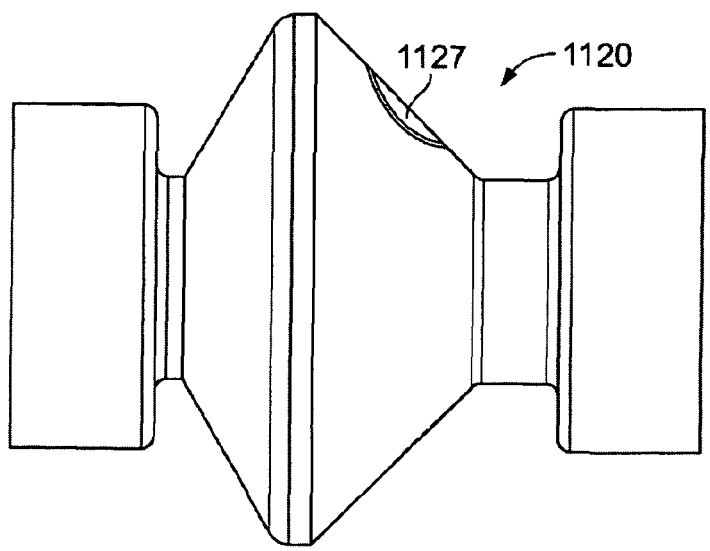
FIG. 7L further illustrates a bellows assembly member defining an aperture for releasing gas or bubbles.

FIG. 7K illustrates these to components separated from each other, but during use, as shown in FIG. 7L, they are attached to each other and rotationally arranged such that the aperture (1127), which extends through the member (1120) and into the inner lumen of the interface valve (1109), is in fluid communication with the port (1126). In this manner, there is a fluid path from the interface valve (1109) lumen, through the aperture (1127), through the port (1126) and to the purge tube (1106b) such that gas/air bubbles within the interface valve (1109) can be released through the aperture (1127) and port (1126) and into the purge line (1106b). This configuration is also useful to permit air that may be trapped within the bellows to be removed by using manual dithering to collapse the bellows and to suction fluid back from flush port (1126).

According to one embodiment, the bellows member (1122), a mono bellows purge port, includes a flush port (1126) attached to a polycarbonate cone. In manufacturing the bellows purge port (1122), a hole punch process may be applied to a pellethane bellow, and the polycarbonate cone to Tygon® interface may be glued with a Dymax® material. According to one embodiment, the cone angle is approximately 30 degrees, and there is a 0.025 inch flat section at the apex of the bellow. The major diameter of one embodiment another bellows member, a mono bellows member (1120), may, for example, be about 0.465 inches. In one embodiment, the left side of the mono bellows member (1120) that is proximal to the catheter splayer (1052) has a shorter trapezoidal bellows section than the right side of the mono bellows (1120), which has a wider trapezoidal bellows section. This asymmetrical construction may encourage trapped air to escape through the purge port bellows member (1122).

If an injection molding process is used, polishing one of the mold surfaces that is used in blow molding results in formation of a non-uniform surface between the original outside diameter of the material as the material is blown or stretched. For example, one surface of the mold is very highly polished to decrease the friction or adhesiveness of the cone material to the mold, thus causing the cone material to flow faster on the smoother mold surface and to grip more on the other surface, resulting in a more uniform wall thickness along desired portions of the bellows.

Figure 7M:
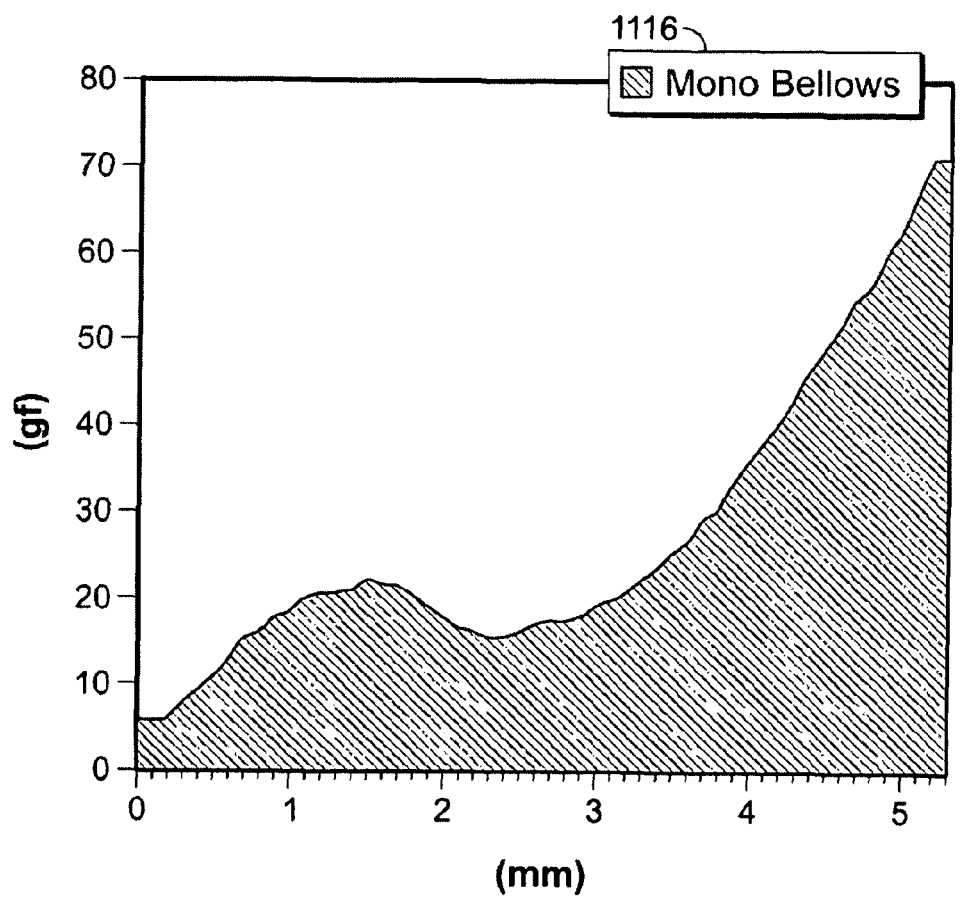
FIG. 7M is a force curve for a bellows component as shown in FIGS. 7J-L.

FIG. 7M illustrates the force curve for one embodiment of the mono bellows assembly (1116). As shown in FIG. 7M, the force (in grams) needed during a dither stroke to a working distance of five millimeters is fairly low and level. FIG. 7M illustrates one example in which the force increases for dither strokes from about 0.2 mm to about 1.5 mm, then decreases slightly, and increases as the dither stroke increases to about 5 mm (force of about 70 grams). In one embodiment of the mono bellows assembly (1116), a rigid polycarbonate backing piece (1122) is glued to the back portion of the bellows (1120) to make that section more rigid and to prevent the bellows from ballooning out when under pressure.

FIGS. 8A-H illustrate methods for flushing the catheter instrument assembly (18) utilizing the components described above with reference to FIGS. 6A-7L. In these figures, arrows indicate the direction of fluid flow.

Figure 8A:
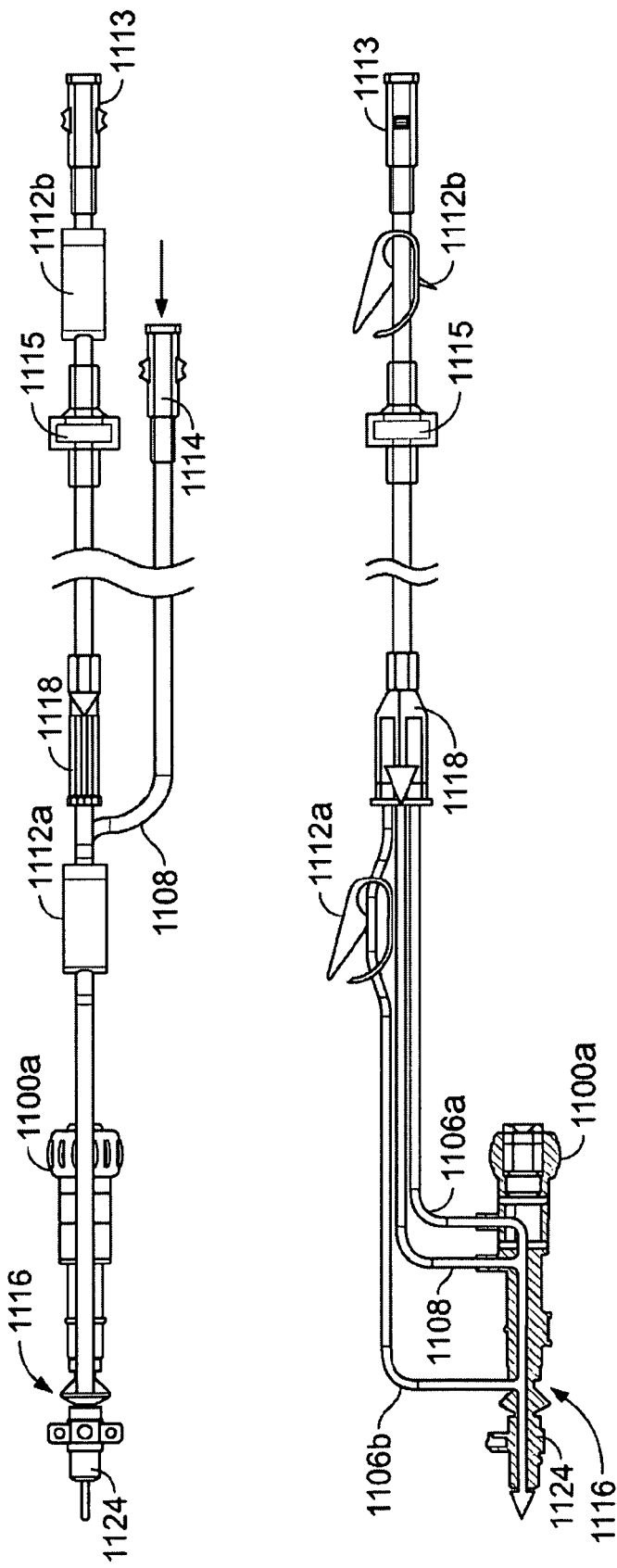
FIGS. 8A-H illustrate methods of flushing a catheter instrument and how clamps are used to control flushing and purging of fluids from the apparatus or valve interface assembly shown in FIGS. 7A-L.

Referring to FIG. 8A, the guide catheter instrument (18) is prepared for use. The two purge lines (1106a,b) extend through a check valve and the contents may be extracted through a syringe, onto a drape, or to anything outside the sterile field. The bellows pinch clamp (1112a) is opened (upper left part of FIG. 8A) and an IV line or other fluid source (1057) is attached to flush port (1114) (upper right part of FIG. 8A). The fastener or Touhy nut (1100a) is tightened (bottom left part of FIG. 8A) and the purge pinch clamp (1112b) is opened (bottom right part of FIG. 8A).

Figure 8B:
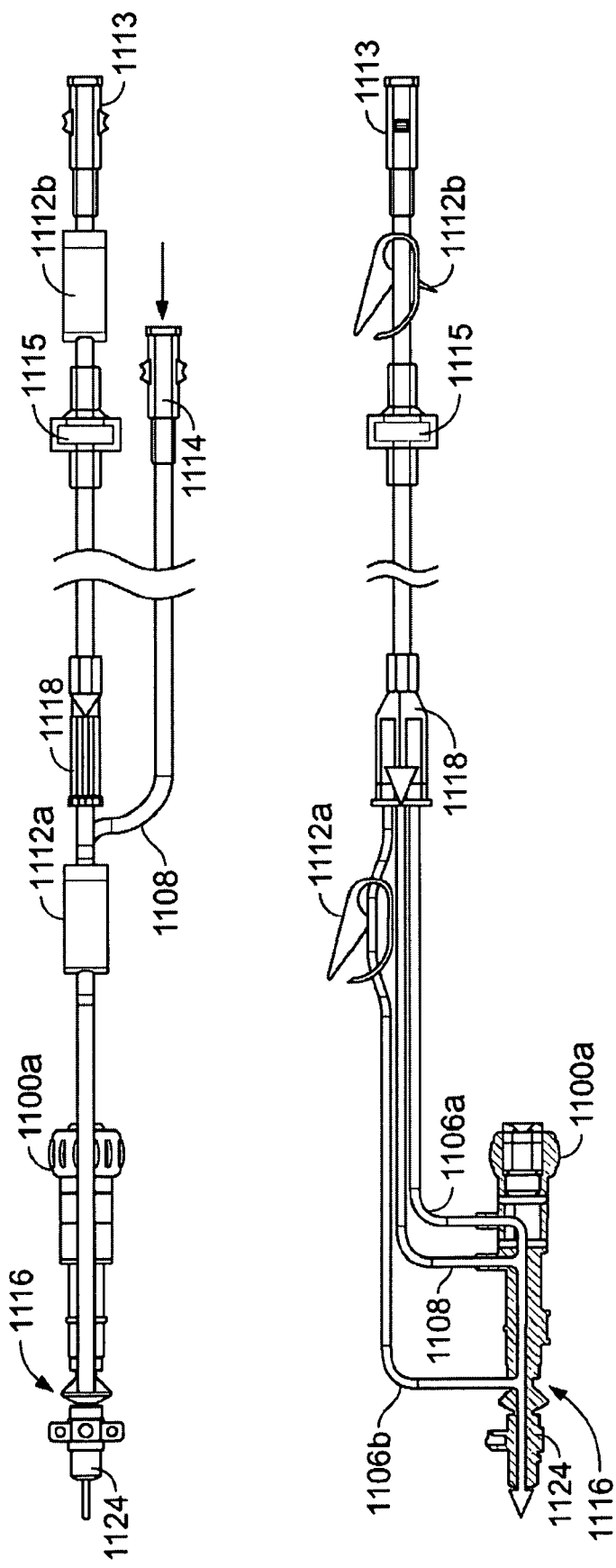

FIG. 8B illustrates the first step of an initial catheter flush process. The IV flow valve is opened (upper right part of FIG. 8B) to allow fluid to enter the catheter system. Saline is introduced through the flush port with both valves open (bottom part of FIG. 8B). Flush fluid is supplied via flush port (1114) and into the interface valve (1109) via flush line (1108) and exits through the purge port (1113) via purge lines (1106a,b) and to the catheter tip via splayer adapter (1124). With the flow restrictor in place, some flow may back feed through the bellows (1116), thus providing adequate flow to clear the bellows (1116).

Figure 8C:
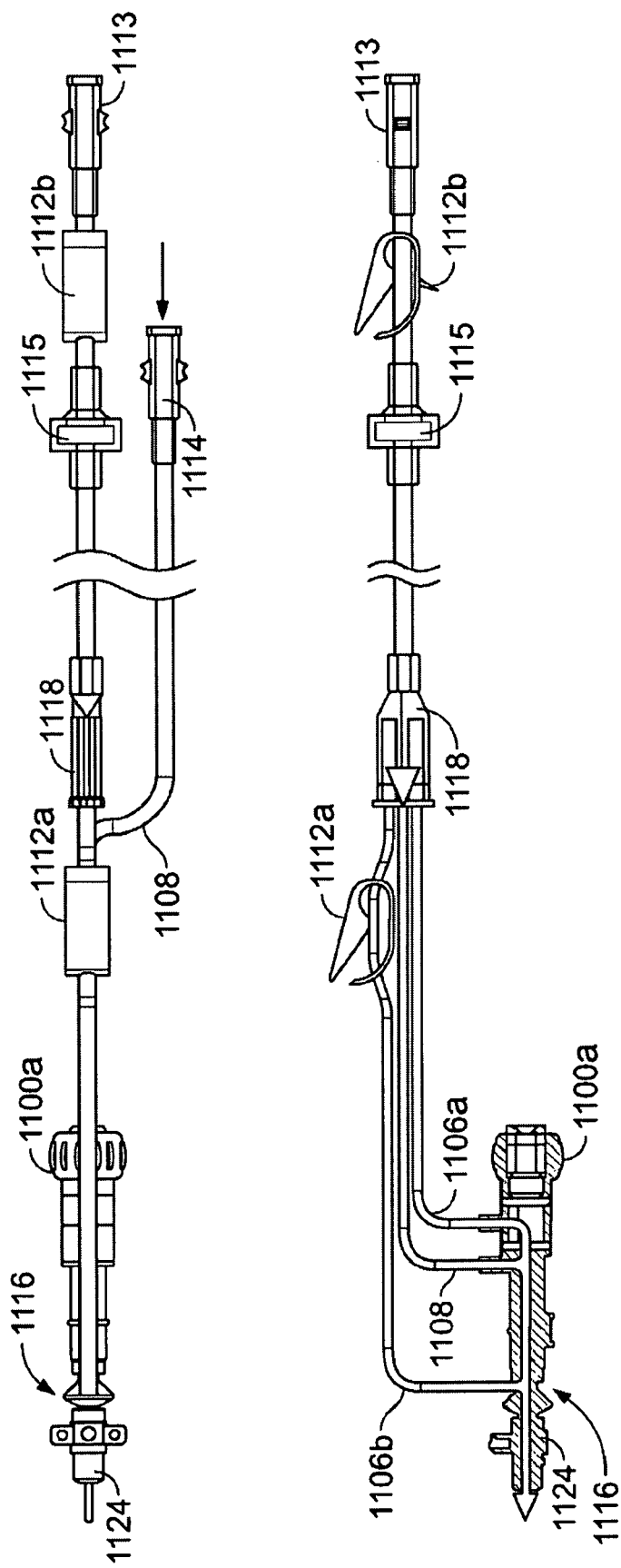

FIG. 8C illustrates a second step of an initial catheter flush process. The flow at the distal tip of the guide catheter (16) is closed off, e.g., with a finger at a tip of the guide catheter (18) (bottom left part of FIG. 8C), but flush fluid is allowed to continue to flow through the purge port (1113) (bottom right part of FIG. 8C).

Figure 8D:
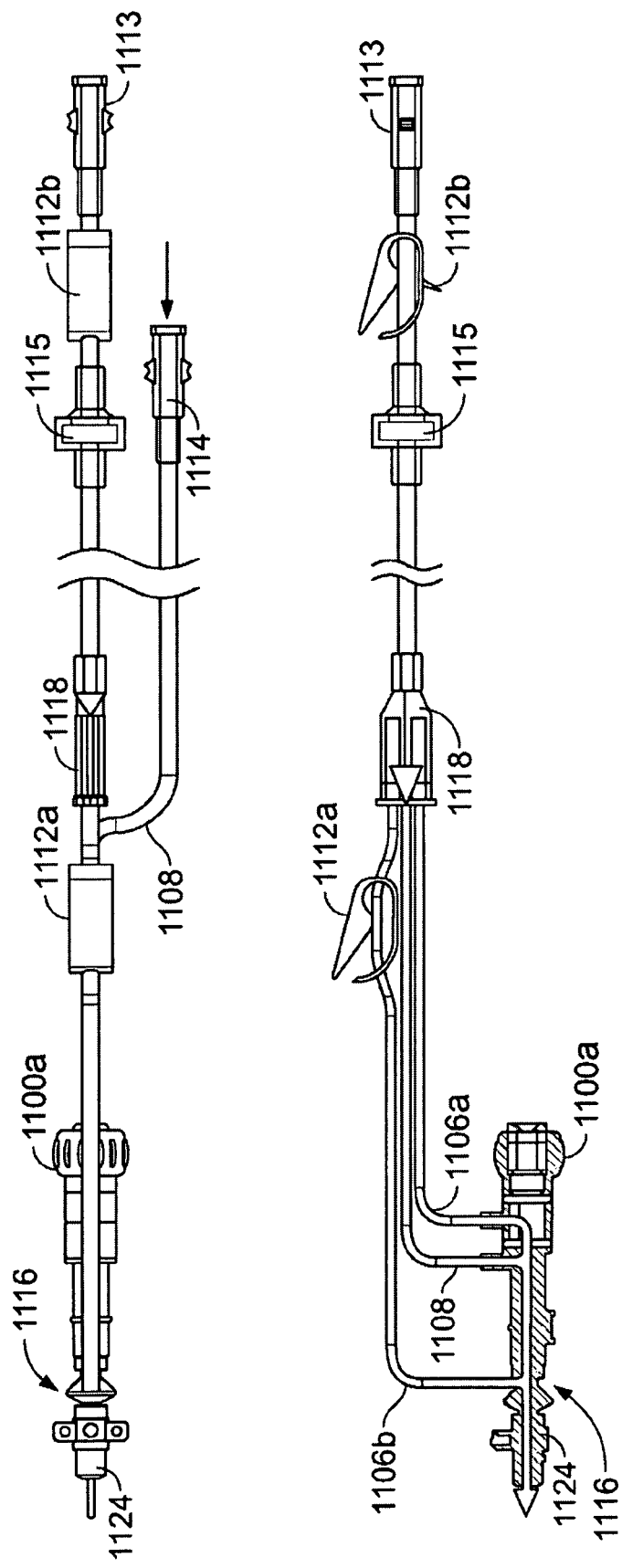

FIG. 8D illustrates a third step of an initial catheter flush process. Once the bellows (1116) is cleared, the pinch clamp (1112a) for the bellows purge port (1122) may be closed (upper left part of FIG. 8D). The bellows pinch valve (1112a) is closed first so that flow through bellows purge line (1106a) is terminated. This increases the flow (upper right part of FIG. 8D) through the interface valve (1109) itself, thus clearing the interface valve body. The purge pinch valve (1112b) is then closed (bottom right part of FIG. 8D) to allow the flow to go distally. After the catheter has been cleared, the flow restrictor may be removed from the distal tip and the catheter is ready for use.

Figure 8E:
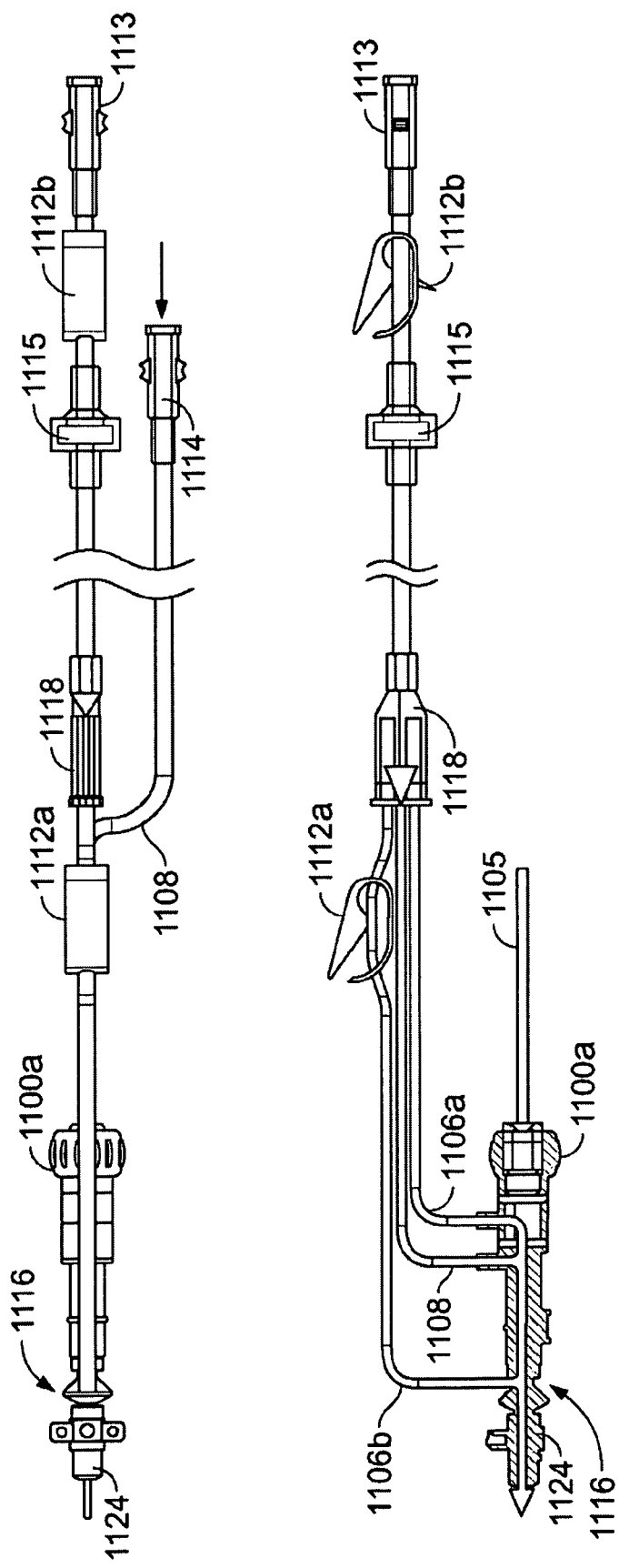

FIG. 8E illustrates the introduction of a working catheter (1105) through the interface valve (1109) of the Touhy assembly (1100). The bellows pinch clamp (1112a) is opened (upper left part of FIG. 8E). Thus, flush fluid (upper right part of FIG. 8E) is allowed to flow through the catheter and the bellows purge line (1106a). The fastener (1100a) is tightened (bottom left part of FIG. 8E) to secure the working catheter (1105) and the purge pinch clamp (1112b) is closed (bottom right part of FIG. 8E).

Figure 8F:
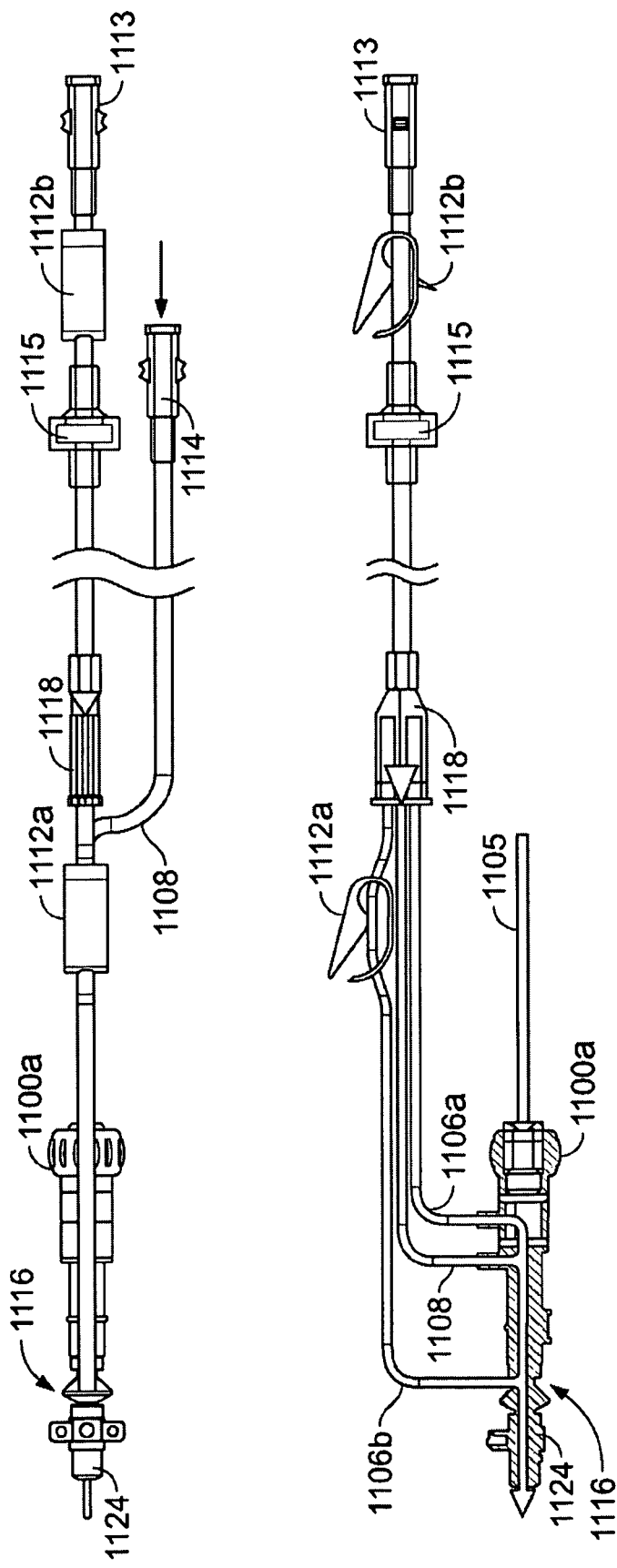

FIG. 8F illustrates one configuration for normal fluid flow through the guide catheter (16) during a surgical procedure. The bellows pinch clamp (1112a) is opened (upper right part of FIG. 8F). The fastener (1100a) is closed or tightened (bottom left part of FIG. 8F) and the purge pinch clamp (1112b) is closed (bottom right part of FIG. 8F). Flush fluid coming in the flush line (1108) is allowed to travel through the interface valve (1109) to the distal tip of the guide catheter (16).

Figure 8G:
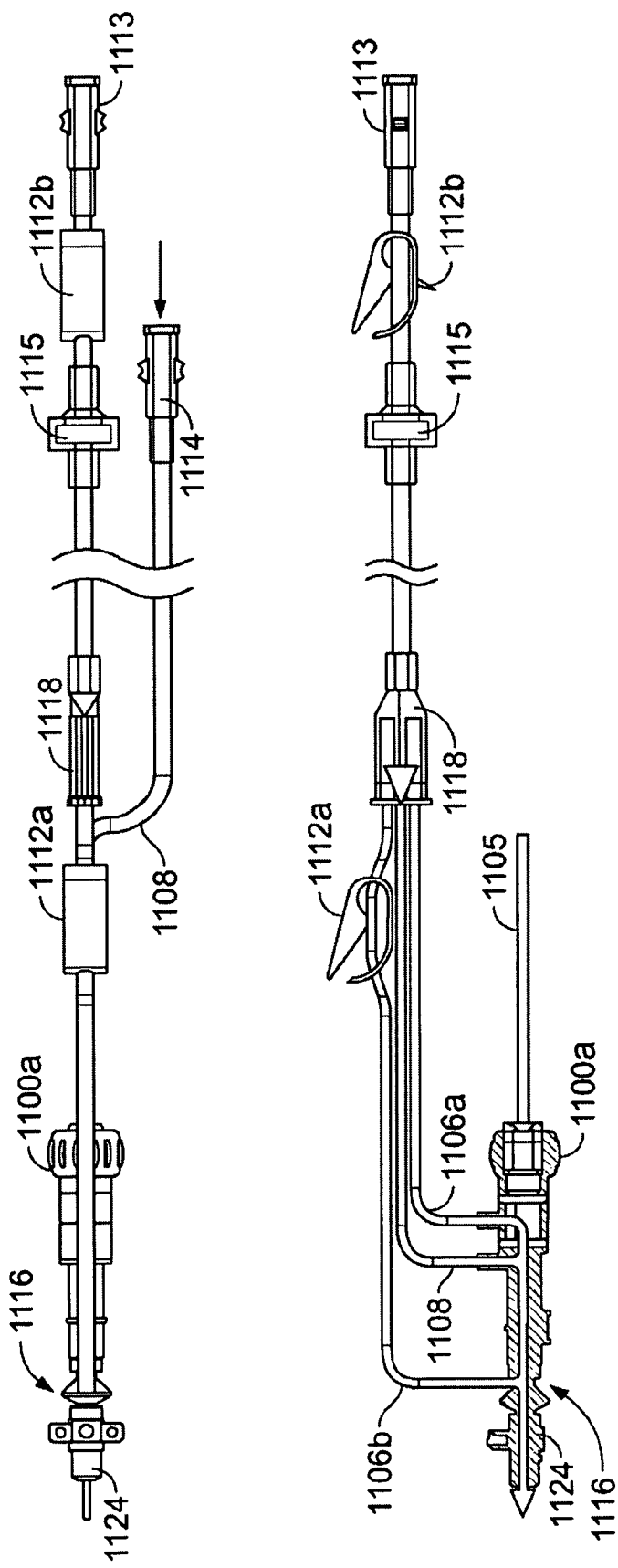
Figure 8H:
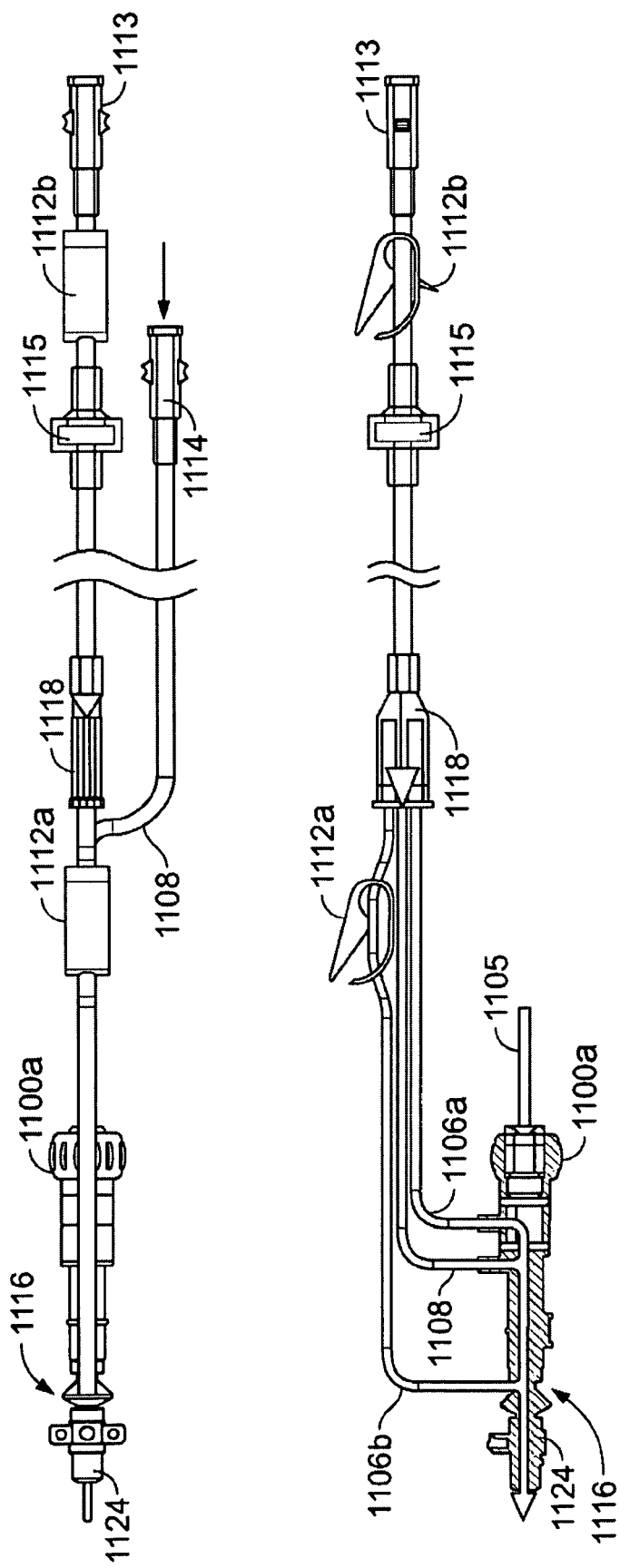

FIG. 8G illustrates the air purging process for the bellows assembly (1116). With flush fluid flowing in from the flush port (1114) (upper right part of FIG. 8G), the bellows pinch clamp (1112a) and the purge port pin clamp are both opened (upper left part and bottom right part of FIG. 8G) so that fluid can flow to the catheter distal tip and through the bellows purge line (1006a) to the purge port (1113).

FIG. 8J illustrates the process for purging air from the interface valve (1109). The saline flush is set to enter the flush port (1114) at a high flow rate (upper right part of FIG. 8H). The bellows pinch clamp (1112a) is closed (upper left part of FIG. 8H) and the purge pinch clamp (1112b) opened. A syringe may be attached to the purge port (1113) to do an assisted push through to push air out or to assist with suctioning out any air bubbles.

One advantage with using embodiments of this assembly (1000) is that the flush process may be performed by a single person whereas other types of assemblies may require more than one person to conduct the flush operation. In addition, any residual air bubbles may be easily removed by opening one or more of the pinch valves (1112a, 1112b) during the flush process. A check valve is also located with the purge line (1106b) to allow flow in a single direction. Thus even if an ablation catheter or other working instrument (1105) was pulled back while a valve was accidentally left open, back flow into the interface valve (1109) of the Touhy assembly (1000) will be prevented.

Although particular embodiments have been shown and described, it should be understood that the above discussion is not intended to limit the scope of these embodiments. While embodiments and variations of the many aspects of the invention have been disclosed and described herein, such disclosure is provided for purposes of explanation and illustration. Many combinations and permutations of the disclosed embodiments are useful in minimally invasive surgery, and the system is configured to be flexible. Thus, various changes and modifications may be made without departing from the scope of the claims Further, because one or more embodiments of the catheter instruments disclosed in above may be used in minimally invasive surgical procedures, the distal portions of these instruments may not be easily visible to the naked eye. As such, various imaging modalities such as magnetic resonance (MR), ultrasound, computer tomography (CT), X-ray, fluoroscopy, etc. may be used to visualize the surgical procedure and progress of these instruments. Furthermore, it may be desirable to know the precise location of any given catheter instrument and/or tool device at any given moment to avoid undesirable contacts or movements. Thus, it is contemplated that one or more localization techniques that are presently available may be applied to any of the apparatuses and methods disclosed above. For example, one or more localization coils may be built into a flexible catheter instrument. In other implementations, a localization technique using radioopaque markers may be used with embodiments of the present invention. Similarly, a fiber optic Bragg sensing fiber may be built into the sidewall of a catheter instrument to sense position and temperature. Furthermore, a plurality of sensors, including those for sensing patient vitals, temperature, pressure, fluid flow, force, etc., may be combined with the various embodiments of flexible catheters and distal orientation platforms disclosed herein.

Further, although certain embodiments are described with reference to an ablation catheter as a working instrument that is inserted through the interface valve and into the central lumen of the catheter instrument, other working instruments may be utilized as needed and depending on the procedure to be performed.

Various implementation and mechanical details may be adjusted or modified as necessary. In one embodiment, the flush line and purge lines are also color coded as are the IV flow restrictors. Further, a Touhy nut or fastener may have a top flange that is increased by 0.020 inches and its thread length increased by a half rotation to allow for retightening. Further, valve assembly components may be made of different materials. In one embodiment, certain assembly components are made of polymer materials, but may also be made of other suitable materials including but not limited to olychloroprene, polycarbonate, silicone, a polycarbonate base, and other suitable materials for use in surgical applications.

What is claimed is:

1. A system for flushing a lumen of a catheter instrument of a robotic surgical system, the system comprising:
   a robotically controllable catheter instrument having a proximal end, a distal end, and defining a lumen;
   a robotically controllable sheath instrument, wherein the catheter instrument is coaxially positioned within the sheath instrument;
   a working instrument;
   an interface valve having a proximal end, a distal end and defining a lumen, the distal end being adapted for attachment to a proximal end of the catheter instrument, and interface valve lumen being configured to receive the working instrument through the interface valve proximal end for insertion into the catheter instrument lumen;
   a fluid supply line coupled to the interface valve, the fluid supply line being in fluid communication with at least a portion of the interface valve lumen;
   a first purge line coupled to the interface valve; and
   a second purge line coupled to the interface valve, wherein the first or second purge lines comprises a valve coupled thereto for controlling fluid flow through the first or second purge line such that fluid flowing into the interface valve lumen can be manipulated to flow in different directions through different portions of the interface valve lumen for evacuation through different purge lines.

2. The system of claim 1, wherein the first and second purge lines are controllable such that fluid flowing into the interface valve lumen can be manipulated to flow in a forward direction towards the catheter instrument and be evacuated through the first purge line, or in a backwards direction away from the catheter instrument and be evacuated through the second purge line.

3. The system of claim 1, wherein the first and second purge lines are controllable such that fluid flowing into the interface valve lumen can be manipulated to flow in a forward direction towards the catheter instrument and be evacuated through the first purge line, and a backwards direction away from the catheter instrument and be evacuated through the second purge line.

4. The system of claim 1, further comprising:
   a first valve coupled to the first purge line to control flow of fluid through the first purge line; and
   a second valve coupled to the second purge line to control flow of fluid through the second purge line.

5. The system of claim 1, the interface valve comprising a valve assembly configured to close a portion of the interface valve lumen when the working instrument is not inserted through the valve assembly.

6. The apparatus of claim 5, the valve assembly comprising:
   a valve body in fluid communication with a purge line;
   an interface member configured to be secured to the valve body; and
   a seal member capable of assuming open and closed states depending on compression of the seal member.

7. The apparatus of claim 6, the valve assembly further comprising:
   a fastener, wherein the fastener is securable to the interface member such that the seal member is disposed between the fastener and the threaded member, wherein the fastener is loosened and the seal member is uncompressed to assume an open state defining an aperture through which the working instrument can be inserted, when the fastener is tightened onto the interface member, the seal member is compressed to assume a closed state and close the aperture such that no working catheter is inserted through the valve assembly.

8. A system for flushing a lumen of a catheter instrument of a robotic surgical system, the system comprising:
   a robotically controllable catheter instrument having a proximal end, a distal end, and defining a lumen;
   a robotically controllable sheath instrument, wherein the catheter instrument is coaxially positioned within the sheath instrument;
   a working instrument;
   an interface valve having a proximal end, a distal end and defining a lumen, the distal end being adapted for attachment to a proximal end of the catheter instrument, and interface valve lumen being configured to receive the working instrument through the interface valve proximal end for insertion into the catheter instrument lumen;
   a fluid line coupled to the interface valve, the fluid line being in fluid communication with at least a portion of the interface valve lumen and configured for bi-directional flushing of the interface valve; and
   a valve coupled to the fluid line for controlling fluid flow and to facilitate bi-directional flushing of the interface valve.

9. The system of claim 8, wherein the fluid line is controllable such that fluid flowing into the interface valve lumen can be manipulated to flow in a forward direction and/or in a backwards direction.

10. The system of claim 8, the interface valve comprising a valve assembly configured to close a portion of the interface valve lumen when the working instrument is not inserted through the valve assembly.

11. The apparatus of claim 10, the valve assembly comprising:
    a valve body in fluid communication with the fluid line;
    an interface member configured to be secured to the valve body; and
    a seal member capable of assuming open and closed states depending on compression of the seal member.

12. The apparatus of claim 11, the valve assembly further comprising:
    a fastener, wherein the fastener is securable to the interface member such that the seal member is disposed between the fastener and a threaded member, wherein the fastener is loosened and the seal member is uncompressed to assume an open state defining an aperture through which the working instrument can be inserted, when the fastener is tightened onto the interface member, the seal member is compressed to assume a closed state and close the aperture such that no working catheter is inserted through the valve assembly.

13. The system of claim 8, wherein the valve is a stopcock.

14. The system of claim 8, wherein a clamp controls the valve.

15. The system of claim 8, further comprising a syringe attached to the fluid line for pushing or pulling fluid through the fluid line.

* * * * *